(12) United States Patent
Fridovich et al.

(10) Patent No.: US 6,916,799 B2
(45) Date of Patent: Jul. 12, 2005

(54) SUBSTITUTED PORPHYRINS

(75) Inventors: Irwin Fridovich, Durham, NC (US); Ines Batinic-Haberle, Durham, NC (US); James D. Crapo, Englewood, CO (US); Brian J. Day, Englewood, CO (US)

(73) Assignees: Duke University, Durham, NC (US); National Jewish Medical and Research Center, Denver, CO (US)

( * ) Notice: Subject to any disclaimer, the term of this patent is extended or adjusted under 35 U.S.C. 154(b) by 0 days.

(21) Appl. No.: 09/880,125

(22) Filed: Jun. 14, 2001

(65) Prior Publication Data

US 2002/0042407 A1 Apr. 11, 2002

Related U.S. Application Data

(63) Continuation of application No. 09/184,982, filed on Nov. 3, 1998, now abandoned.
(60) Provisional application No. 60/064,116, filed on Nov. 3, 1997.

(51) Int. Cl.[7] .................... C07D 487/22; A61K 31/409; A61K 31/555; A61P 11/06
(52) U.S. Cl. ........................ 514/183; 514/184; 514/185; 540/145
(58) Field of Search ................................. 514/183, 184, 514/185; 540/145

(56) References Cited

U.S. PATENT DOCUMENTS

| | | | |
|---|---|---|---|
| 2,951,799 A | 9/1960 | Sharp ......................... 204/162 |
| 4,614,723 A | 9/1986 | Schmidt | |
| 4,657,902 A | 4/1987 | Kappas et al. .............. 514/185 |
| 4,746,735 A | 5/1988 | Kruper, Jr. et al. | |
| 4,758,422 A | 7/1988 | Quay | |
| 4,829,984 A | 5/1989 | Gordon ....................... 600/12 |
| 4,837,221 A | 6/1989 | Bonnett | |
| 4,851,403 A | 7/1989 | Picker et al. | |
| 4,866,054 A | 9/1989 | Dori et al. .................. 514/184 |
| 4,885,114 A | 12/1989 | Gordon et al. ............. 252/589 |
| 4,892,941 A | 1/1990 | Dolphin et al. | |
| 4,895,719 A | 1/1990 | Radhakrishnam | |
| 4,963,367 A | 10/1990 | Ecanow | |
| 5,010,073 A | 4/1991 | Kappas et al. .............. 514/185 |
| 5,051,337 A | 9/1991 | Sakoda et al. | |
| 5,087,438 A | 2/1992 | Gordon ......................... 424/9 |
| 5,109,016 A | 4/1992 | Dixon et al. ................ 514/410 |
| 5,130,245 A | 7/1992 | Marklund et al. | |
| 5,162,519 A | 11/1992 | Bonnett | |
| 5,169,630 A | 12/1992 | Okaya et al. | |
| 5,171,680 A | 12/1992 | Mullenbach et al. | |
| 5,192,757 A | 3/1993 | Johnson et al. ............. 514/185 |
| 5,192,788 A | 3/1993 | Dixon et al. ................ 514/410 |
| 5,202,317 A | 4/1993 | Bruice | |
| 5,217,966 A | 6/1993 | Bruice | |
| 5,223,538 A | 6/1993 | Fridovich | |
| 5,227,405 A | 7/1993 | Fridovich | |
| 5,236,914 A | 8/1993 | Meunier | |
| 5,236,915 A | 8/1993 | Fiel | |
| 5,248,603 A | 9/1993 | Marklund et al. | |
| 5,262,532 A | 11/1993 | Tweedle et al. | |
| 5,277,908 A | 1/1994 | Beckman et al. .......... 424/94.4 |
| 5,281,616 A | 1/1994 | Dixon et al. | |
| 5,284,647 A | 2/1994 | Niedballa | |
| 5,366,729 A | 11/1994 | Marklund et al. | |
| 5,403,834 A | 4/1995 | Malfroy-Camine et al. . 514/185 |
| 5,405,369 A | 4/1995 | Selman et al. ................ 607/88 |
| 5,472,691 A | 12/1995 | Marklund et al. | |
| 5,493,017 A | 2/1996 | Therien et al. | |
| 5,563,132 A | 10/1996 | Bodaness ..................... 514/185 |
| 5,599,924 A | 2/1997 | Therien et al. ............. 540/145 |
| 5,604,199 A | 2/1997 | Funanage ....................... 514/6 |
| 5,610,293 A | 3/1997 | Riley et al. ................. 540/470 |
| 5,637,578 A | 6/1997 | Riley et al. ................. 514/183 |
| 5,674,467 A | 10/1997 | Maier et al. ............... 424/1.65 |
| 5,747,026 A | 5/1998 | Crapo ........................ 424/94.3 |
| 5,767,272 A | 6/1998 | Wijesekera et al. ......... 540/145 |
| 5,834,509 A | 11/1998 | Malfroy-Camine et al. . 514/492 |
| 5,874,421 A | 2/1999 | Riley et al. ................. 514/161 |

(Continued)

FOREIGN PATENT DOCUMENTS

| | | |
|---|---|---|
| EP | 0 127 797 | 12/1984 |
| EP | 0 186 962 | 7/1986 |
| EP | 0 282 899 | 9/1988 |
| EP | 0 336 879 | 10/1989 |
| EP | 0 337 601 | 10/1989 |
| EP | 0 345 171 | 12/1989 |
| EP | 0 414 915 A1 | 3/1991 |
| EP | 0 462 836 | 12/1991 |
| EP | 0 524 161 A1 | 1/1993 |
| EP | 0 532 327 | 3/1993 |
| FR | 2 676 738 | 11/1992 |
| WO | 91/04315 | 4/1991 |
| WO | WO 91/04315 | 4/1991 |
| WO | WO 91/19977 | 12/1991 |
| WO | 92/07935 | 5/1992 |
| WO | WO 92/08482 | 5/1992 |
| WO | WO 92/15099 | 9/1992 |
| WO | WO 93/02090 | 2/1993 |
| WO | WO 94/04614 | 3/1994 |
| WO | WO 94/05285 | 3/1994 |

(Continued)

OTHER PUBLICATIONS

Davila et al. {J. Chem. Soc. Chem. Commun., (1987), 525–527}.*
Bütje et al. {Inorg. Chim. Acta, 167 (1990) 97–108}.*
Sari et al. {Biochemistry, 29, (1990), 4205–4215}.*

(Continued)

Primary Examiner—James O. Wilson
Assistant Examiner—Kahsay Habte
(74) Attorney, Agent, or Firm—Nixon & Vanderhye P.C.

(57) ABSTRACT

The present invention relates, in general, to a method of modulating physiological and pathological processes and, in particular, to a method of modulating cellular levels of oxidants and thereby processes in which such oxidants are a participant. The invention also relates to compounds and compositions suitable for use in such methods.

32 Claims, 11 Drawing Sheets

U.S. PATENT DOCUMENTS

| | | | |
|---|---|---|---|
| 5,948,771 A | 9/1999 | Danziger | 514/185 |
| 5,976,498 A | 11/1999 | Neumann et al. | 424/9.1 |
| 5,976,551 A | 11/1999 | Mottez et al. | 424/195.11 |
| 5,994,339 A | 11/1999 | Crapo et al. | |
| 5,994,410 A | 11/1999 | Chiang et al. | 514/709 |
| 6,013,241 A | 1/2000 | Marchal et al. | 424/1.65 |
| 6,046,188 A | 4/2000 | Malfroy-Camine et al. | 514/185 |
| 6,060,467 A | 5/2000 | Buelow et al. | 514/185 |
| 6,084,093 A | 7/2000 | Riley et al. | 540/465 |
| 6,087,493 A | 7/2000 | Wheelhouse et al. | 540/145 |
| 6,103,714 A | 8/2000 | Fridovich et al. | 514/185 |
| 6,127,356 A | 10/2000 | Crapo et al. | 514/185 |
| 6,180,620 B1 | 1/2001 | Salvemini | 514/184 |
| 6,204,259 B1 | 3/2001 | Riley et al. | 514/184 |
| 6,214,817 B1 | 4/2001 | Riley et al. | 514/186 |
| 6,245,758 B1 | 6/2001 | Stern et al. | 514/185 |
| 6,372,727 B1 | 4/2002 | Crow et al. | 514/81 |
| 6,395,725 B1 | 5/2002 | Salvemini | 514/184 |
| 6,403,788 B1 | 6/2002 | Meunier et al. | 540/145 |
| 6,417,182 B1 | 7/2002 | Abrams et al. | 514/185 |
| 6,544,975 B1 | 4/2003 | Crapo et al. | |
| 6,548,045 B2 | 4/2003 | Sakata et al. | |
| 6,566,517 B2 | 5/2003 | Miura et al. | |
| 6,602,998 B2 | 8/2003 | Kobuke et al. | |
| 6,624,187 B1 | 9/2003 | Pandey et al. | |
| 2002/0058643 A1 | 5/2002 | Cherian et al. | 514/78 |

FOREIGN PATENT DOCUMENTS

| | | |
|---|---|---|
| WO | WO 95/10185 | 4/1995 |
| WO | WO 95/31197 | 11/1995 |
| WO | WO 96/09038 | 3/1996 |
| WO | WO 96/09053 | 3/1996 |
| WO | WO 96/40223 | 12/1996 |
| WO | WO 97/06824 | 2/1997 |
| WO | WO 97/06830 | 2/1997 |
| WO | WO 97/06831 | 2/1997 |
| WO | WO 97/33588 | 9/1997 |
| WO | WO 97/33877 | 9/1997 |
| WO | WO 98/33503 | 6/1998 |
| WO | WO 98/58636 | 12/1998 |
| WO | WO 99/23097 | 5/1999 |
| WO | WO 99/55388 | 11/1999 |
| WO | WO 00/04868 | 2/2000 |
| WO | WO 00/43395 | 7/2000 |
| WO | WO 00/72893 | 12/2000 |
| WO | WO 01/26655 | 4/2001 |
| WO | WO 01/96345 | 12/2001 |

OTHER PUBLICATIONS

Comhair et al. (Medline abstract) and Rosenfeld et al. (Medline abstract).*

Vodizinskii et al. (Russ. J. Org. Chem. 34(6) 1998, 882–885.*

Kaufmann et al. {Inorg. Chem. 34, (1995), 5073}.*

Hambright {J. Inorg. Nucl. Chem. 39, (1997), 1102}.*

Hambright et al. {Porphyrin Chem. Adv., Pap. Porphyrin Symp. (1979), Meeting Date 1977, 284–92}.*

Batinic–Haberle et al, "The *Ortho* Effect Makes Manganese(III) Meso–Tetrakis–(N–Methylpyridinium–2–yl)Porphyrin a Powerful and Potentially Useful Superoxide Dismutase Mimic", The Journal of Biological Chemistry 273(38):24521–24528 (1998).

Inoue et al, "Expression of a Hybrid Cu/Zn–type Superoxide . . . " J. Bio. Chem., vol. 266. No. 25. pp. 16409–16414 (1991).

Day et al. "Manganic Porphyrins Possess Catalase Activity . . . ," Arch. Biochem. Biophys., vol. 347. No. 2. pp. 256–262 (1997).

Tsan. M–F., "Superoxide Dismutase and Pulmonary Oxygen Toxicity." XP–002074505, pp. 286–290.

Naruta et al. (1991) J. Am. Chem. Soc. 113:3595–3596.

Leondiadis et al. (1989) J. Org. Chem. 54:6135–6138.

Foran et al. "Effect of Electrolyte Concentration on Axial Anion Ligation in Manganese(III) meso–Tetraphenylporphyrin Chlorides". Inorg. Chem. 31:1463–1470 (1992).

Milgrom, Facile Aenal Oxidation of a Porphyrin. Part 3. Some Metal Complexes of meso–Tetrakis–(3, 5–di–t–butyl–4–hydroxyphenyl)porphyrin. J. Chem. Soc. Perkin Trans. 11:71–79 (1988).

Bockhorst and Hoehn–Bertage, "An Optimized Synthesis of Manganese mesoTetra(4–sulfonato–phenyl)porphine: A Tumor–Selective MRI Contrast Agent", Tetrahedron 50(29):8657–8660 (1994).

Keinan et al, "Catalytic Antibodies. Circular Dichroism and UV–Vis Studies of Antibody–Metalloporphyrin Interactions". Inorg. Chem. 31:5433–5438 (1992).

Marx, "Role of Gene Defect in Heredity ALS Clarified", Science 261:986 (1993).

Epp et al, "Superoxide Dismutase Activity of Manganese Chelates", 76–78 (1986).

Bors et al, "An expanded function for superoxide dismutase", Chemical Abstracts 115:388 (1991), Abstract No. 109185h.

Miigrom et al, "Redox Behaviour of Phenolic Porphyrins in Basic Solutions: A Reappraisal", Free Rad. Res. 24(1):19–29 (1996).

Szabo et al, "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", FEBS Letters 381:82–86 (1996).

Patel et al, "Requirement for Superoxide in Excitotoxic Cell Death", Neuron 16:345–355 (1996).

Bamford et al, "The Squalestatins: Synthesis and Biological Activity of Some C3–Modified Analogues; Replacement of a Carboxylic Acid or Methyl Ester with an Isoelectric Heterocyclic Functionality", J. Med. Chem. 38:3502–3513 (1995).

Szabo et al, "Peroxynitrite is involved in the Pathogenesis of the Vascular Contractile and Energetic Failure in Endotoxic Shock", Shock Society Meeting (1996).

Stralin et al, "Effects of Oxidative Stress on Expression of Extracellular Superoxide Dismutase. CuZn–Superoxide Fibroblast". Biochem. J. 298:347–352 (1994).

Folz et al, "Extracellular Superoxide Dismutase (SOD3): Tissue–Specific Expression, Genomic Characterization, and Computer–Assisted Sequence Analysis of the Human EC SOD Gene". Genomics 22:162–171 (1994).

Clyde et al, "Distribution of Manganese Superoxide Dismutase mRNA in Normal and Hyperoxic Rat Lung". American Journal of Respiratory Cell and Molecular Biology 8:530–537 (1993).

Wolberg et al, Electrocical and Electron Paramagnetic Resonance Studies of Metallocoronyms and Thier Electrochemical Oxidation Products:, Journal of the American Chemical Society 92(10):2982–2990 (1970).

Pasternack et al, "Superoxide Dismutase Activities of an Iron Porphyrin and Other Iron Complexes". Journal of the American Chemical Society 101(4):1026–1031 (1979).

Winkelman, James. "The Distribution of Tetraphenylporphinesulfonate in the Tumor–bearing Rat". Cancer Research 22:589–596 (1962).

Moisy et al. "Catalytic Oxidation of 2,5–Di–Terbutylphenol by Molecular Oxygen Electroassisted by Poly(PyrroleManganese–Porphyrin)". New J. Chem. 13:511–514 (1989).

Malinski et al. "Characterization of Conductive Polymeric Nickel(II) Tetrakis(3–methoxy–4–hydroxy–phenyl)Porphyrin as an Anodic Material for Electrocatalysis". J. Electrochem. Soc. 138(7):2008–2015 (1991).

Weinraub et al, "Chemical properties of water–soluble porphyrins. 5. Reactions of some manganese (III) porphyrins with the superoxide and other reducing radicals". Int. J. Radiat. Biol. 50(4):649–658 (1986) (Abs).

Fajer et al, "π–Cation Radicals and Dications of Metalloporphyrins". Journal of the American Chemical Society 92(11):3451–3459 (1970).

Pasternack et al, "Aggregation of Nickel(II), Coppwer (II), and Zinc(II) Derivatives of Water–Soluble Porphyrins", Inorganic Chemistry 12(11):2606–2610 (1973).

Datta–Gupta et al, "Synthetic Porphyrins. I. Synthesis and Spectra of Some *para*–Substituted *meso*–Tetraphenylporphines (1)", J. Heterocycl. Chem. 3:495–502 (1966).

Harriman et al. "Photochemistry of Manganese Porphyrins Part 2.–Photoreduction". pp. 1543–1552.

Longo et al, "The Synthesis and Som e Physical Properties of *ms*–Tetra(pentafluorophenyl)–porphin and *ms*–Tetraphenylporphines (1)". Notes 6:927–931 (1969).

Barnitz Mc Laughlin et al, "Reactions of $Fe^{10}(meso-\alpha,\alpha,\alpha,\alpha-tetrakis[C-(N-methylisonicotinamido)phenyl]porphyrin)^{5-}$ and $Fe^{10}(meso$–tetrakis[N–methylcyridinium–4–yl]porphyrin$)^{5-}$ with NC, $CO_2$, and $O_2^-$". Inorg. Chem. 32:941–947 (1993).

Pasternack et al, "On the Aggregation of Meso–Substituted Water–Soluble Porphyrins", Journal of American Chemical Society 94(13):4511–4517 (1972).

Datta–Gupta et al, "Synthetic Porphyrins II Preparation and Soectra of Some Metal Chelates of *para*", Journal of Substituted–*mesa*–Tetraphenylporphines. Journal of Pharmaceutical Science 57(2):300–304 (1968).

Boissinot et al, "Rational Design and Expression of a Heparin–Targeted Human Superoxide Dismutase", Biochemical and Biophysical Research Communication 190(1):250–256 (1993–.

Oury et al, "Cold–induced Brain Edema in Mice", The Journal of Biological Chemistry 268(21):15394–15398 (1993).

Oury et al, "Extracellular superoxide dismustase, nitric oxide, and central nervous system $O_2$ toxicity", Proc. Natl. Acad. Sci. USA 89:9715–9719 (1992).

Pasternack et al, "Catalyst of the Disproportionation of Superoxide by Metalloporphyrins III", Journal of Inorganic Biochemistry 15:261–267 (1981).

Oury et al, "Establishment of Transgenic Mice Expressing Human Extracellular Superoxide Dismutase", American Review of Respiratory Disease 143(4):A515 (1991), International Conference Supplement Abstracts—No. 236.

Oury et al, "Transgenic Mice Superexpressing Human Extracellular Superoxide Dismutase Show Increased Resistance to Cold–induced Brain Edema, But are More Susceptible to Hyperbaric Oxygen", American Review of Respiratory Disease 145(4):A713 (1992), International Conference Supplement Abstracts—No. 211.

Oury et al, "Immunocytochemical Localization of Extracellular Superoxide Dismutase in Human Lung", American Review of Respiratory Disease 147(4):A713 (1993), International Conference Supplement Abstracts—No. 246.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the Graduate School of Duke University (Jun. 17, 1993).

Gosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691–4699 (1995).

De Peretti et al, "Imidazol[2,1–b]benzoxazole–3–acetamide derivatives, their preparation, and their therapeutic use", Chemical Abstracts 121:1016, Abstract No. 121:200896u.

Oberley et al, "Anticancer activity of metal compounds with superoxide dismutase activity", Agents and Actions 15(5/6):535–538 (1984).

Collman et al, "Synthesis of "Face to Face" Porphyrin Dimers Linked by 5,15–Substituents: Potential Binuclear Multielectron Redox Catalysts", J. Am. Chem. Soc. 103:516–533 (1981).

Gassman et al, "Electronic Effects of Peripheral Substituents in Porphyrins: X–ray Photoelectron Spectroscopy and ab Initio Self–Consistent Field Calculations", J. Am. Chem. Soc. 114:9990–10000 (1992).

Bishop et al, "The Reaction of Thiomides with Phosphorus Ylides", J. Org. Chem. 56:5079–5091 (1991).

Picker et al, "Cobalt(III) complexes of water soluble synthetic meso–substituted porphyrins as radiation sensitizers for oxic and hypoxic tumor cells". 8–Radiation 112:405 (1990) Abstract No. 112:73026d.

McCord et al, "Superoxide Dismutase–An Enzymic Function for Erythrocuprein". Biochemistry 492, p. 346.

McCord et al, Superoxide Dismutase An Enzymic Function for Erythrocuprein (Hemocuprein), The Journal of Biological Chemistry 244(22):6049–6055 (1969).

Crapo et al, "Superoxide Dismutase and Oxygen Toxicity", Clinical Research, p. 222.

Crapo et al, "The Failure of Aerosolized Superoxide Dismutase to Modify Pulmonary Oxygen Toxicity", American Review of Respiratory Disease 115:1027–1033 (1977).

Joester et al, "Superoxide Dismutase Activity of $Cu^{2-}$–Amino Acid Chelates", FEBS Letters 25(1):25–28 (1972).

Brigeiius et al, "Superoxide Dismutase Activity of Low Molecular Weight Cu2+–Chelates Studied by Pulse Radiolysis". FEBS Letters 47(1):72–75 (1974).

Sorenson, John R.J., "Copper Chelates as Possible Active Forms of the Antiarthritic Agents", Journal of Medicinal Chemistry 19(1):135–148 (1976).

deAlvare et al, "Mechanism of Superoxide Anion Scavenging Reaction by Bis–(Salicylato)–Copper(II) Complex" Biochemical and Biophysical Research Communications 69(3):687–694 (1976).

Halliwell, Barry, "The Superoxide Dismutase Activity of Iron Complexes", FEBS Letters 56(1):34–38 (1975).

McClune et al, "Catalysis of Superoxide Dismutation by Iron–Ethylenediaminetetraacetic Acid Complexes. Mechanism of the Reaction and Evidence for the Direct Formation of an Iron(III)–Ethylenediaminetetraacetic Acid Peroxo Complex from the Reaction of Superoxide with Iron(II)–Ethylenediaminetetraacetic Acid", Communications to the Editor, p. 5220–5222 (1977).

Diguiseppi et al, "Putative Superoxide Dismutase Activity of Iron–EDTA: A Reexamination", Archives of Biochemistry and Biophysics 203(1):145–150 (1980).

Robertson, Jr. et al, "Does Copper–D–Peniciilamine Catalyze the Dismutation of $O_2$ ?", Archives of Biochemistry and Biophysics 203(2):830–831 (1980).

Werringloer et al, "The Integration of Divalent Copper and the Microsomal Electron Transport System". The Journal of Biological Chemistry, 254(23):11839–11846 (1979).

Pasternack et al, "Catalyst of the Disproportionation of Superoxide by Metalloporphyrins", Journal of Inorganic Biochemistry 11:261–267 (1979).

Archibald et al, Manganese and Defenses against Oxygen Toxicity in *Lactobacillus plantarum*, Journal of Bacteriology 145(1):442–451 (1981).

Archibald et al, Manganese Superoxide Dismutase, Oxygen Tolerance in Some Lactic Acid Bacteria. Journal of Bacteriology 146(3):928–936 (1981).

Archibald et al, The Scavenging of Superoxide Radical by Manganous Complex: In Vitro, Archives of Biochemistry and Biophysics 214(2):452–463 (1982).

Archibald et al, Investigations of the State of the Manganese in *Lactobacillus plantarum*, Archives of Biochemistry and Biophysics 215(2):589–596 (1982).

Darr et al, "A Mimic of Superoxide Dismutase Activity Based Upon Desferrioxamine B and Manganese(IV)", Archives of Biochemistry and Biophysics 258(2):351–355 (1987).

Beyer, Jr., Characterization of a Superoxide Dismutase Mimic Prepared from Desferrioxamine and $MnO_2$, Archives of Biochemistry and Biophysics 271(1):149–156 (1989).

Faulkner et al, "Characterization of Mn(III) Complexes of Linear and Cyclic Desferrioxamines as Mimics of Superoxide Dismutase Activity", Archives of Biochemistry and Biophysics 310(2):341–346 (1994).

Faulkner et al, Stable Mn(III) Porphyrins Mimic Superoxide Dismutase in Vitro and Substitute for It in Vitro, The Journal of Biological Chemistry 269(38):23471–23476 (1994).

Liochev et al, "A Cationic Manganic Porphyrin Inhibits Uptake of Paraquat by *Escherichia coli*", Archives of Biochemistry and Biophysics 321(1):271–275 (1995).

Peretz et al, "Chemical properties of water–soluble porphyrins 3. The reaction of superoxide radicals with some metalloporphyrins". Int. J. Radiat. Biol. 42(4):449–456 (1982).

Baudry et al, "Salen–Manganese Complexes are Superoxide Dismutase–Mimics", Biochemical and Biophysical Research Communication 192(2):964–968 (1993).

Gonzalez et al, "EUK–8, a Synthetic Superoxide Dismutase and Catalase Mimetic, Ameliorates Acute Lung Injury in Endotexemic Swine", The Journal of Pharmacology and Experimental Therapeutics 275(2):798–806 (1995).

Deune et al, "Prevention of Ischemia–Reperfusion Injury with a Synthetic Metalloprotein Superoxide Dismutase Mimic, SC52608", Plastic and Reconstructive Surgery 98(4):711–718 (1996).

Lowe et al, "Comparison of the cardiovascular effects of two novel superoxide dismutase mimetics, SC–55858 and SC–54417, in conscious dogs", European Journal of Pharmacology 304:81–86 (1996).

Weiss et al, "Manganese–based Superoxide Dismutase Mimetics Inhjibit Neutral Infiltration in Vitro", The Journal of Biological Chemistry 271(42):26149–26156 (1996).

Jin et al, "A new route to water soluble porphyrins: phosphonium and ammonium type cationic porphyrins and self–assembly", Chem. Commun., pp. 1939–1940 (1996).

Pitié et al, "Oxidation at Carbon–1' of DNA Deoxyriboses by the Mn–TMPyP/KHSO5 System Results from a Cytochrome P–450–Type Hydroxylation Reaction", J. Am. Chem. Soc. 117:2935–2936 (1995).

Libby et al, "Cationic Porphyrin Derivatives As Inhibitors of Polyamine Catabolism", Biochemical Pharmacology 50(9):1527–1530 (1995).

Ilan et al, "Superoxide Dismuting Activity of an Iron Porphyrin", Inorg. Nucl. Chem. Letters 17(3/4):93–96 (1981).

Solomon et al, "Chemical properties of Water–Soluble Porphyrins. 2. The Reaction of Iron(III) Tetrakis(4–N–methylpyridyl)porphyrin with the Superoxide Radical Dioxygen Couple", J. Phys. Chem. 86:1842–1849 (1982).

Weinraub et al, "Chemical Properties of Water–Soluble Porphyrins. 1. Equilibria between Some Ligands and Iron(III) Tetrakis (4–*N*–methylpyridyl)porphyrin", J. Phys. Chem. 86:1839–1842 (1982).

Day et al, "A Metalloporphyrin Superoxide Dismutase Mimetic Protects Against Paraquat–Induced Endothelial Cell Injury, in Vitro". The Journal of Pharmacology and Experimental Therapeutics 275(3):1227–1232 (1995).

Kariya et al, "Superoxide Dismutase (SOD) Activity with Fe–chlorin e6–Na and Suppression of Malignant Tumor Growth in Rats". Cancer Biotheraphy 10(2):139–145 (1995).

Liochev et al, A Cationic Manganic Porphyrin Inhibits Uptake of Paraquat by *Escherichia Coli*. Archives of Biochemistry and Biophysics 321(1):271–275 (1995).

Ohkawa et al, "Assay for Lipid Peroxides in Animal Tissues by Thiobarbituric Acid Reaction", Analytical Biochemistry 95:351 (1979).

Yue et al, "Carvedilol, a New Vasodilator and Beta Adrenoceptor Antagonist, is an Antioxidant and Free Radical Scavenger", The Journal of Pharmacology and Experimental Therapeutics 263:(1992).

Song et al, "Anti–HIV activities of anionic metalloporphyrins and related compounds", Antiviral Chemistry and Chemotherapy 8(2):85 (1996).

Harriman and Porter, "Photochemistry of Manganese Porphyrins", J. Chem. Soc. 275:1532–1542 (1979).

Bedioui et al, "Metalloporphyrin–Polypyrrole Film Electrode: Characterization and Catalytic Application", J. Electroanal. Chem. 207:87–99 (1986).

Ruoslahti et al, "Arg–Gly–Asp: A Versatile Cell Recognition Signal", Cell 44:517–518 (1986).

Kumar et al. "Radioprotection by Antioxidant Enzymes and Enzyme Mimetics", Pharmac. Ther. 39:301–309 (1988).

Weiss et al, "Evaluation of Activity of Putative Superoxide Dismutase Mimics". The Journal of Biological Chemistry 2638(31):23049–23054 (1993).

Parge et al, "Atomic structures of wild–type and thermostable mutant recombinant human Cu,Zn superoxide dismutase", Proc. Natl. Acad. Sci. USA 89:6109–6113 (1992).

Lappin, "Part III Bioinorganic Studies", Inorganic Reaction Mechanisms 7:334–343 (1981).

Schlogen et al Reactivity of Unsubstituted Porphyrin, German version Angew Chem. 87:388 (1975).

Wheelhouse et al, "Cationic Porphyrins as Telomerase Inhibitors: the Interaction of Tetra–(N–methyl–4–pyridyl)porphine with Quadruplex DNA", J. Am. Chem. Soc. 120:3261–3262 (1998).

Madakyan et al, "New water–soluble metal complexes of meso–tetrakis[3–N–(2$^1$–hydroxyethyl)pyridyl]porphyrins and their pharmacological activity", Chem. Abstract 113:653 (1990)—Abstract No. 114907h.

Sharma et al, "Synthesis of amphiphilic 5–(4–N–alkylpyridiniumyl)–10, 15,20–triphenylporphyrins and their aggregational properties in different solvent systems", Chemical Abstracts vol. 123(1) (1995)—Abstract No. 9222.

Schneider et al, "Ligand–Porphyrin Complexes: Quantitative Evaluation of Stacking and Ionic Contributions". J. Org. Chem. 59:7464–7472 (1994).

Giradeau et al, "Substituent Effects in the Electroreduction of Porphyrins and Metalloporphyrins", J. Am. Chem. Soc. 101(14):3857–3862 (1979).

Crapo et al, 721195, Document No. 123:218443 (1995).

Sheldon, Chapter I in Metalloporphyrins in Catalytic Oxidations, Marcel Dekker, Inc. (1994).

Butje et al, Inorg. Chim. Acta 167:97–108 (1990).

Davila et al, J. Chem. Soc. Chem. Commun., pp. 353–527 (1987).

Hambright, J. Inorg. Nucl. Chem. 39:1102–1103 (1977).

Kaufmann et al, Inorg. Chem. 24:5073 (1995).

Sari et al, Biochemistry 29:4205–4215 (1990).

Vodzinskii et al, Russ. J. Org. Chem. 34(6):882–885 (1998).

Hambright et al, Porphyrin Chem. Adv. [Pap. Porphyrin Symp.] (1979), meeting date 1977, pp. 284–292, editor: Longo.

Shlozer et al, Angew. Chem. Internat. Edit. 14(5):363 (1975).

Comhair et al, Lancet 355(9204):624 (2000) (Medline abstract).

Rosenfield et al, Pediatrics 6:811–817 (1996) (Medline abstract).

Zahedi, "Semiempirical molecular orbital calculations of biliverdin: study of dynamics and energetics of the self–association of a two–electron oxidation product", Theochem. 531:79–88 (2000).

Lord, "Redox characteristics of nickel and palladium complexes of the open–chain tetrapyrrole octaethylbilindione: a biliverdin model", Inorg. Chem. 39(6):1128–1134 (2000).

Balch, "Isolation and characterization of an iron biliverdin–type complex that is formed along with verdohemochrome during the coupled oxidation of iron (II) octaethylporphyrin", Am. Chem. Soc. 115(20):9056–9061 (1993).

Koerner, "Carbon monoxide production during the oxygenation of cobalt complexes of linear tetrapyrroles", Inorg. Chem. 37(50):982–988 (1998).

Balch, "Solid–state self–association of the two–electron oxidation product of a biliverdin analogue", J. Chem. Soc. Chem. Commun. 6:643–644 (1995).

Balch, "Geometric and electronic structure and dioxygen sensitivity of the copper complex of octaethylbilindione, a biliverdin analog", J. Am. Chem. Soc. 115(25):12206–12207 (1993).

Spasojevic and Batinic–Haberle, "Manganese(III) complexes with porphyrins and related compounds as catalytic scavengers of superoxide", Inorganica Chimica Acta 317:230–242 (2001).

Mackensen et al, "Neuroprotection from Delayed Postischemic Administration of a Metalloporphyrin Catalytic Antioxidant", The Journal of Neuroscience 21(13):4582–4592 (2001).

Hunt et al, "Amphiphilic peroxynitrite decomposition catalysts in liposomal assemblies", Chemistry & Biology 4(11):845–858 (1997).

Dwyer et al, "Protective Properties of Tin– and Manganese–Centered Porphyrins Against Hydrogen Peroxide–Mediated Injury in Rat Astroglial Cells", J. Neurochem 71:2497 (1998).

O'hara et al, "Potentiation of radiation–induced cell kill by synthetic metalloporphyrins", Int. J. Radiat. Oncol. Biol. Phys. 16(4):1049–1052 (1989).

Lee et al, "Rapid decomposition of peroxynitrite by manganese porphyrin–antioxidant redox couples", Bioorganic & Medical Chemistry Letters 7(22):2913–2918 (1997).

Lee and Smith, "Syntheses of symmetrically substituted 5–alkyl– and 5–aryl–dihydrodipyrrins and of porphyrins and bisporphyrins therefrom", J. Chem. Soc. Perkin Trans 1:1215–1227 (1997).

Madakyan et al, "Some metal complexes of meso–tetrakis (3–N–substituted pyridyl) porphyrins and their bioactivity", Arm. Khim. Zh. 42(10):642–646 (1989).

Batinic–Haberle et al, "A Potent Superoxide Dismutase Mimic" Manganese[B] Octabromo–meso–tetrakis–(N–methylpyridinium–4–yl)Porphyrin, Archives of Biochemistry and Biophysics 343(2):225–233 (1997).

Crapo and Tierney, "Superoxide dismutase and pulmonary oxygen toxicity", Am. J. Physiol. 226:1401–1407 (1974).

Tjahjono et al, "Cationic porphyrins bearing diazolium rings: synthesis and their interaction with calf thymus DNA", Biochemica et Biophisica Acta 1472:333–343 (1999).

Collot and Schaeffer, "Ring contraction of homoporphyrins to porphyrins, meso–Reactivity of 5,10,15–Triphenylporphin and Porphin", J. Chem. Research (S):51 (1978).

Elangovan and Krishnan, "Photophysical properties of porphyrin amphiphiles bearing pyridinium alkyl groups", Chemical Physics Letters 194(1,2):139–146 (1992).

Madakyan et al, "Some metal complexes of meso–tetrakis(3–N–substituted pyridyl)porphyrins and their bioactivity", Arm. Khim. Zh. 42(10):642–646 (1989).

Hambright, Peter, "An acid solvolysis kinetic study of manganese(II)–tetra(2–N–methylpyridyl)porphine", J. Inorg. Chem. 39:1102–1103 (1977).

Vergeldt et al, "Intramolecular Interactions in the Ground and Excited State of Tetrakis(N–methylpyridyl)porphyrins", J. Phys. Chem. 99:4397–4405 (1995).

Louati et al, "Homophophyrines: Effets D'Une Coupure De Conjugaison Cyclique Sur La Reactivite Redox Des Porphyrines", Nouv. J. Chim. 2:163–168 (1978).

Yu and Su, "Electrocatalytic reduction of nitric oxide by water–soluble manganese porphyrins", Journal of Electroanalytical Chemistry 368:323–327 (1994).

Hambright et al, "Synthesis and Characterization of New Isomeric Water–Soluble Porphyrins Tetra(2-N-methylpyridyl)porphine and Tetra(3-N-methylpyridyl)porphine", Inorganic Chemistry 15(9):2314–2315 (1976).

Batinic–Haberle et al, Relationship among Redox Potentials, proton Dissociation Constants of Pyrrolic Nitrogens, and In Vivo and in Vitro Superoxide Dismutating Activities of Manganese(III) and Iron(III) Water–Soluble Porphyrins, Inorg. Chem. 38:4011–4022 (1999).

Batinic–Haberle et al, "Manganese(III) meso–tetrakis(ortho–N–alkylpyridyl)porphyrins. Synthesis, characterization, and catalysis of $O_2$ dismutation", J. Chem. Soc., Dalton Trans. pp. 2689–2696 (2002).

Kobayashi et al, "Oxidative Stress Relief for Cancer–Bearing Hosts by the Protein–Bound Polysaccharide of Coriolus versicolor QUEL with SOD Mimicking Activity", Cancer Biotherapy 9(1):55 (1994).

Richards et al, "Observation of a Stable Water–Soluble Lithium Porphyrin", Inorg. Chem. 35:1940–1944 (1996).

Batinic–Haberle et al, "The Ortho Effect Makes Manganic Meso–Tetrakis–(N–Methylpyridinium–2–YL) (MnTM–2–PyP$^{5+}$) A Powerful And Useful Superoxide Dismutase Mimic", Oxygen '97, The 4$^{th}$ Annual Meeting of The Oxygen Society, Council Meeting, The Palace Hotel, San Francisco, California Nov. 20–24, 1997, p. 38, Abstract 1–8.

Laehdesmaeki et al, "Detection of Oxygen Consumption of Cultured Adherent Cells by Bead Injection Spectroscopy", Analytical Chemistry 71(22):5248–5252 (1999).

Vinogradov and Wilson, "Palladium catalyzed carbonylation of Br–substituted porphyrins", Tetrahedo nLetters 39(49):8935–8938 (1998).

Walker et al, "Models of the cytochromes b. 5. EPR Studies of low–spin iron(III) tetraphenylporphyrins", Journal of the American Chemical Society 106(23):6888–6898 (1984).

Falk, "Contributions to the chemistry of pyrrolic pigments", Tetrahedron 37(4):761–767 (1981).

Burke, "Photochemical and thermal transformations of phytochrome", Chem. Physiol. Bile Pigm., Int. Symp., pp. 509–517 (1975).

Lindsey et al, "Rothemund and Adler–Longo Reactions Revisited: Synthesis of Tetraphenylphorins under Equilibrium Conditions", J. Org. Chem. 52:827–836 (1987).

Lindsey et al, "$^{252}$CF Plasma Desorption Mass Spectrometry in the Synthesis of Porphyrin Model Systems", Anal. Chem. 64(22):2804–2814 (1992).

Tsvetkov et al, "Infrared spectra of copper complexes of tetraphenylporphyrin", Izvestiya Vysshikh Uchebnykh Zavedenij, Khimiya I Khimicheskaya Tekhnologiya 27(7)):782–785 (1984) –English Abstract.

Berezin et al, Effect of Ligand structure on the kinetic stability of tetraphenylporphyrin complexes of zinc and cadmium, Zhurnal Neorganicheskoi Khimii 25(10):2645–2652 (1980) –English Abstract.

Berezin et al, "Factors determining the stability of complexes of copper with p–substituted derivatives of tetraphenylporphine", Zhurnal Fizicheskoi Khimil 53(11):2716–2719 (1979) –English Abstract.

Wang et al, Structure of LB film of 5, 10, 15,20–tetra-(p–ethoyycarbonphenyl)porphyrin, Yingyong Huaxue 10(2):87–88 (1993) –English Abstract.

Gauuan et al, "Superoxide dismutase mimetics: synthesis and structure–activity relationship study of MnTBAP analogues", Bioorganic & Medicinal Chemistry 10(9):3013–3021 (2002).

Lindsey et al, "Synthesis of tetraphenylporphyrins under very mild conditions", Tetrahedron Letters 27(41):4969–4970 (1986).

* cited by examiner

MECHANISM

MnTE-2-PyP$^{5+}$     $X_1 = X_2 = X_3 = X_4 = H$

MnCl$_1$TE-2-PyP$^{5+}$     $X_1 = Cl$, $X_2 = X_3 = X_4 = H$

MnCl$_{2a}$TE-2-PyP$^{5+}$     $X_1 = X_2 = Cl$, $X_3 = X_4 = H$

MnCl$_3$TE-2-PyP$^{5+}$     $X_1 = X_2 = X_3 = Cl$, $X_4 = H$

MnCl$_4$TE-2-PyP$^{5+}$     $X_1 = X_2 = X_3 = X_4 = Cl$

Metalloporphyrins

Trolox (+)-Rutin

US 6,916,799 B2

SUBSTITUTED PORPHYRINS

This application is a continuation of application Ser. No. 09/184,982, filed Nov. 3, 1998, now abandoned, which claims the benefit of Provisional application Ser. No. 60/004,116, filed Nov. 3, 1997.

TECHNICAL FIELD

The present invention relates, in general, to a method of modulating physiological and pathological processes and, in particular, to a method of modulating cellular levels of oxidants and thereby processes in which such oxidants are a participant. The invention also relates to compounds and compositions suitable for use in such methods.

BACKGROUND

Oxidants are produced as part of the normal metabolism of all cells but also are an important component of the pathogenesis of many disease processes. Reactive oxygen species, for example, are critical elements of the pathogenesis of diseases of the lung, the central nervous system and skeletal muscle. Oxygen free radicals also play a role in modulating the effects of nitric oxide (NO·). In this context, they contribute to the pathogenesis of vascular disorders, inflammatory diseases and the aging process.

A critical balance of defensive enzymes against oxidants is required to maintain normal cell and organ function. Superoxide dismutases (SODs) are a family of metalloenzymes that catalyze the intra- and extracellular conversion of $O_2^-$ into $H_2O_2$ plus $O_2$, and represent the first line of defense against the detrimental effects of superoxide radicals. Mammals produce three distinct SODs. One is a dimeric copper- and zinc-containing enzyme (CuZn SOD) found in the cytosol of all cells. A second is a tetrameric manganese-containing SOD (Mn SOD) found within mitochondria, and the third is a tetrameric, glycosylated, copper- and zinc-containing enzyme (EC-SOD) found in the extracellular fluids and bound to the extracellular matrix. Several other important antioxidant enzymes are known to exist within cells, including catalase and glutathione ceroxidase. While extracellular fluids and the extracellular matrix contain only small amounts of these enzymes, other extracellular antioxidants are also known to be present, including radical scavengers and inhibitors of lipid peroxidation, such as ascorbic acid, uric acid, and α-tocopherol (Halliwell et al, Arch. Biochem. Biophys. 280:1 (1990)).

The present invention relates generally to low molecular weight porphyrin compounds suitable for use in modulating intra- and extracellular processes in which superoxide radicals, or other oxidants such as hydrogen peroxide or peroxynitrite, are a participant. The compounds and methods of the invention find application in various physiologic and pathologic processes in which oxidative stress plays a role.

SUMMARY OF THE INVENTION

The present invention relates to a method of modulating intra- or extracellular levels of oxidants such as superoxide radicals, hydrogen peroxide, peroxynitrite, lipid peroxides, hydroxyl radicals and thiyl radicals. More particularly, the invention relates to a method of modulating normal or pathological processes involving superoxide radicals, hydrogen peroxide, nitric oxide or peroxynitrite, using low molecular weight antioxidants, and to methine (ie, meso) substituted porphyrins suitable for use in such a method. The substituted porphyrins are also expected to have activity as antibacterial and antiviral agents, and as ionophores and chemotherapeutics. Objects and advantages of the present invention will be clear from the description that follows.

Numbers 0–4 correspond to x in $MnCl_xTE\text{-}2\text{-}PyP^{5+}$ Corresponding data for one active site of Cu,Zn-SOD (Ellerby et al, J. Am. Chem. Soc. 118:6556 (1996)).

Figure 7A:
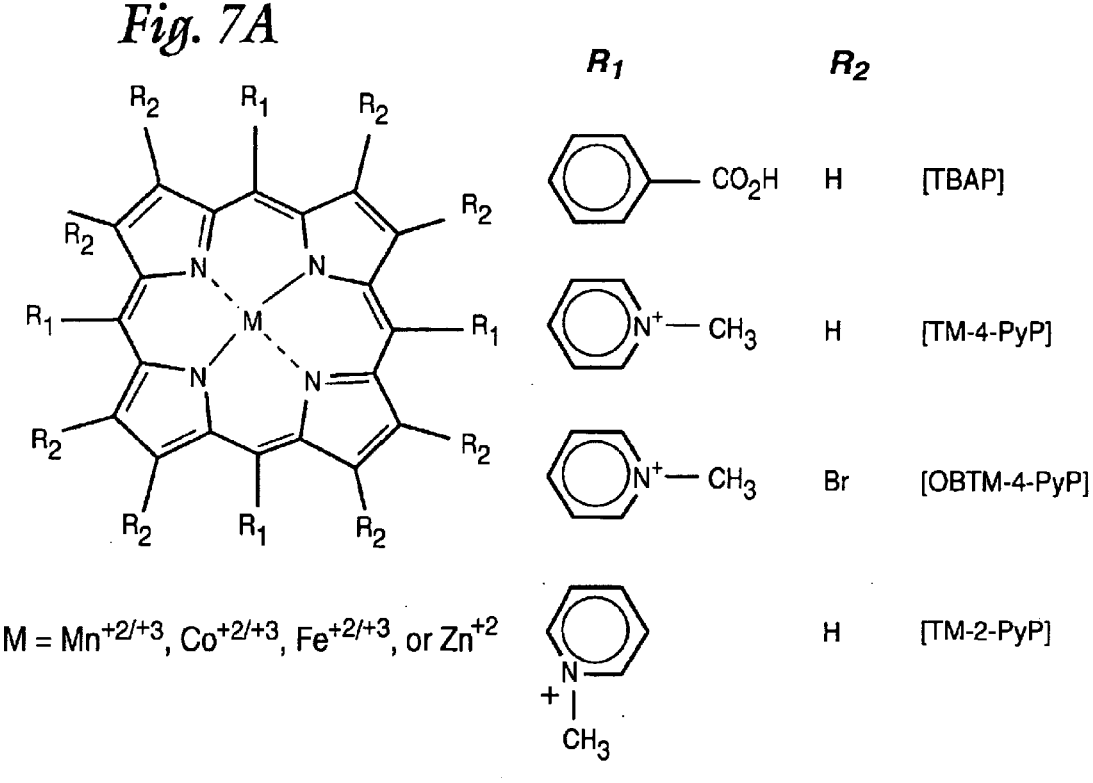
Figure 7B:
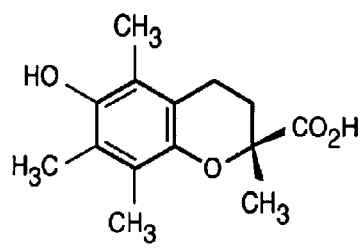
Figure 7C:
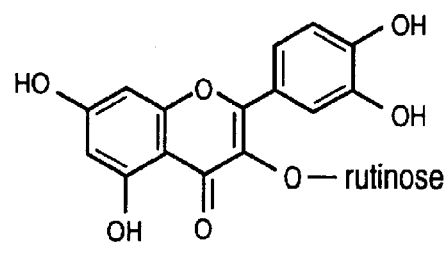

FIG. 7. Illustrated are the chemical structures of three classes of antioxidants. A) The meso-porphyrin class is depicted where: $R_1$ is either a benzoic acid (tetrakis-(4-benzoic acid) porphyrin (TBAP)) or a N-methyl group in the 2 or 4 position of the pyridyl (tetrakis-(N-methyl pyridinium-2(4)-yl) porphyrin (TM-2-PyP, TM-4-PyP)); $R_2$ is either a hydrogen (H) or a bromide (Br, OBTM-4-PyP) and where the porphyrin is ligated with either a manganese (Mn), cobalt (Co), iron (Fe), or zinc (Zn) metal. B) The vitamin E analog class is represented by trolox. C) The flavanoid class is represented by rutin.

Figure 8:
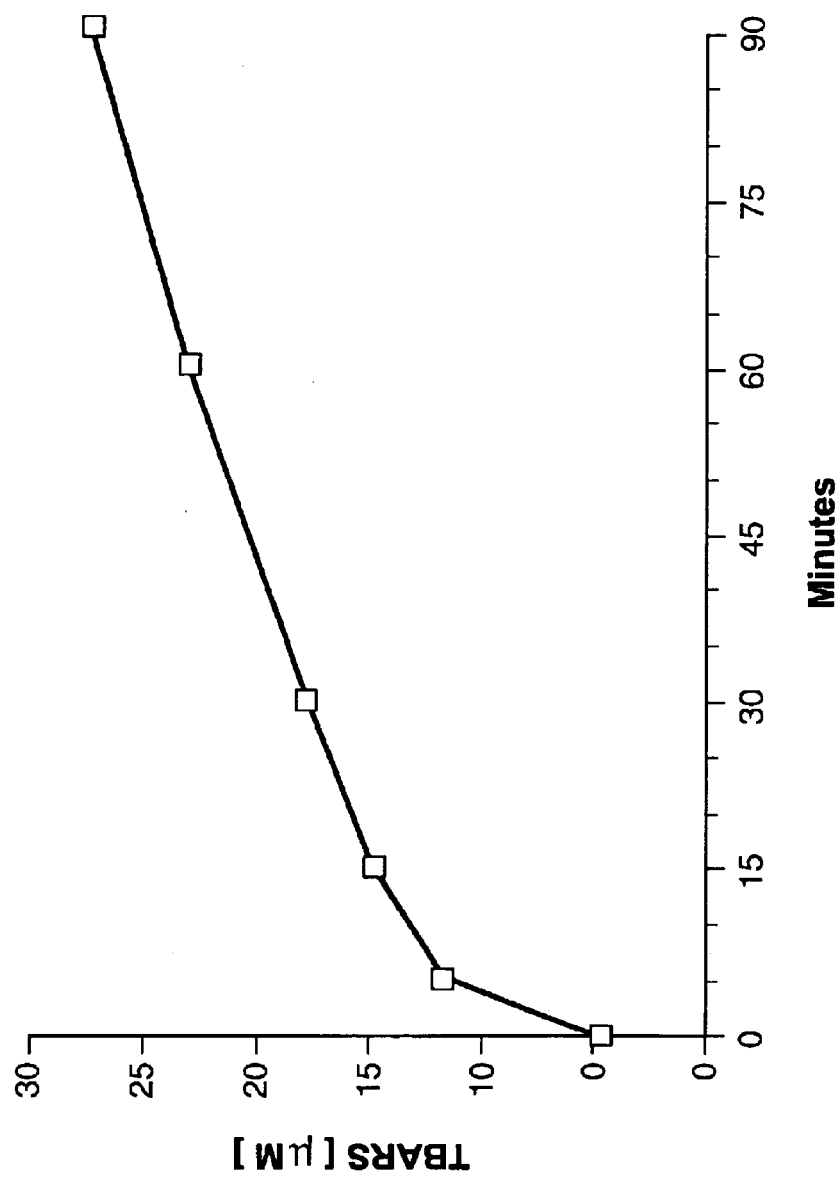

FIG. 8. The time course of iron/ascorbate mediated oxidation of rat brain homogenates. Rat brain homogenates were incubated for various times with 0.25 μM $FeCl_2$ and 1 μM ascorbate, and lipid peroxidation was measured as thiobarbituric acid reactive species (TBARS) spectrophotometrically at 535 nm (n=3).

Figure 9:
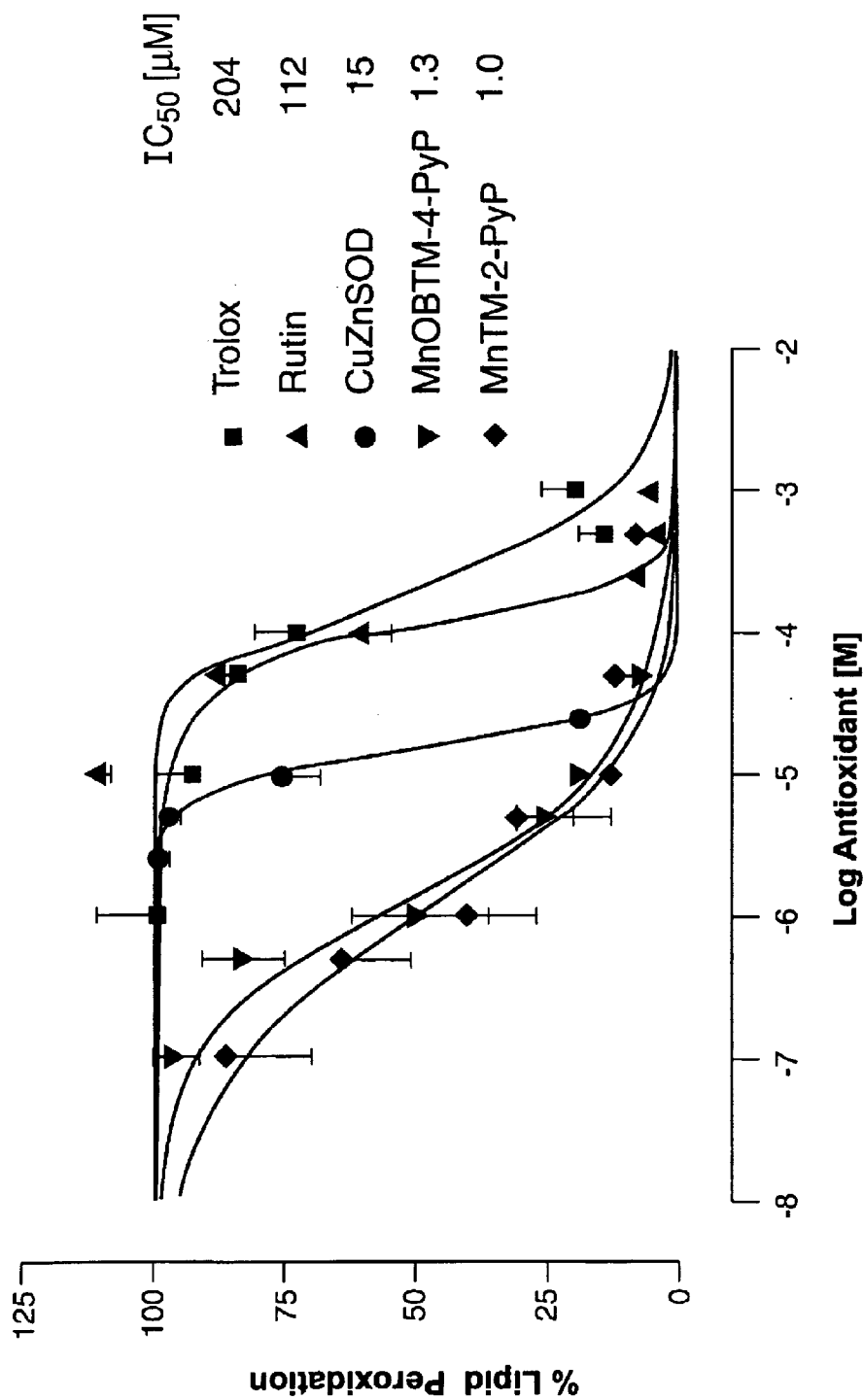

FIG. 9. The comparison of trolox (■), rutin (▲), bovine CuZnSOD (●), MnOBTM-4-PyP (▼) and MnTM-2-PyP (♦) in their ability to inhibit iron/ascorbate mediated oxidation of rat brain homogenates. Rat brain homogenates were incubated for 30 minutes with 0.25 μM $FeCl_2$ and 1 μM ascorbate, and lipid peroxidation was measured as thiobarbituric acid reactive species. The amount of TBARS formed in 30 minutes was expressed as 100% lipid peroxidation (n=3–6). Sigmoidal dose response curves were derived from fitting the data to a non-linear regression program.

Figure 10:
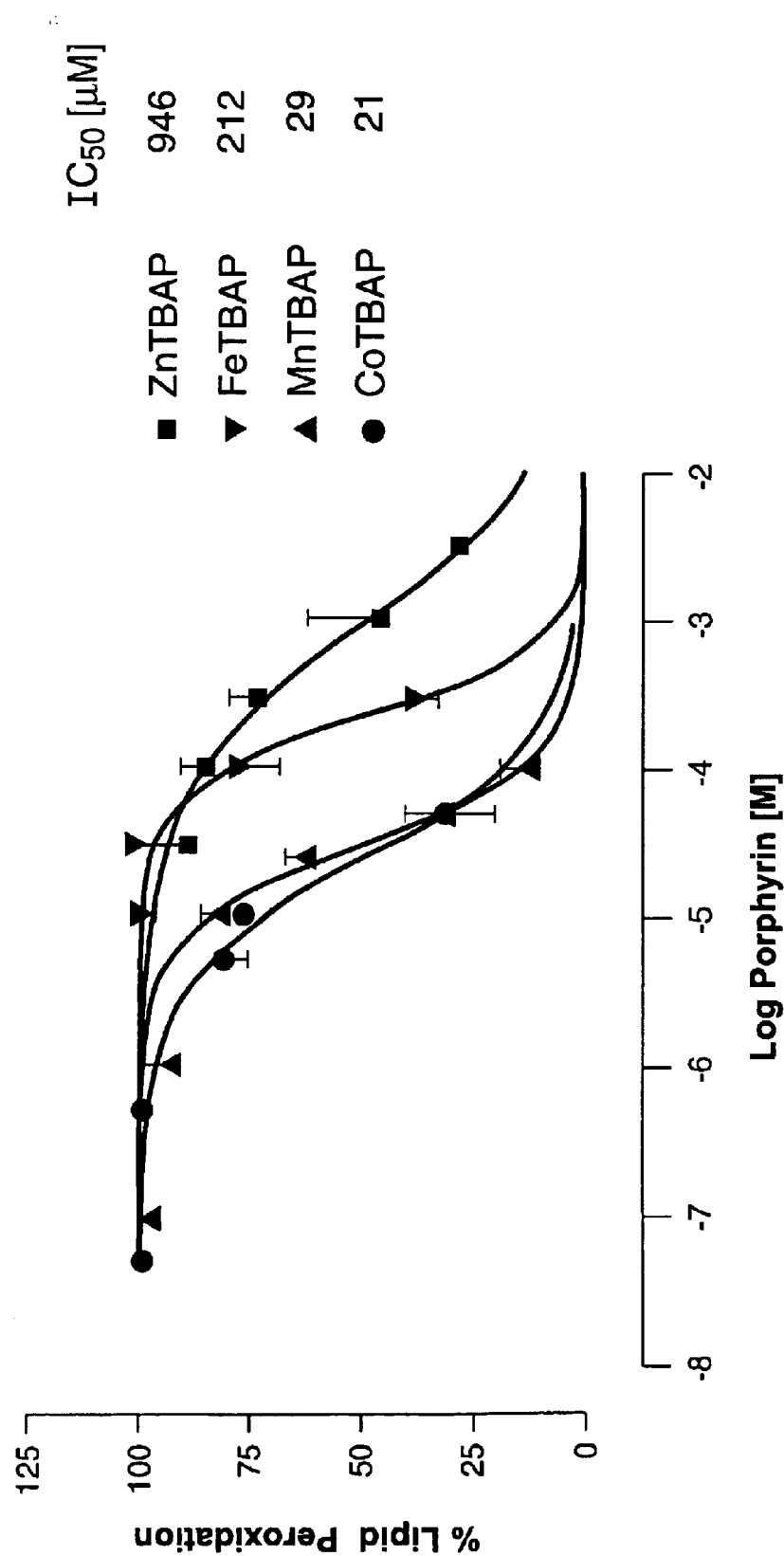

FIG. 10. The comparison of manganic (▲), cobalt (●), iron (▼) and zinc (■) analogs of TBAP in their ability to inhibit iron/ascorbate mediated oxidation of rat brain homogenates. Rat brain homogenates were incubated for 30 minutes with 0.25 μM $FeCl_2$ and 1 μM ascorbate, and lipid peroxidation was measured as thiobarbituric acid reactive species. The amount of TBARS formed in 30 minutes was expressed as 100% lipid peroxidation (n=3–6). Sigmoidal dose response curves were derived from fitting the data to a non-linear regression program.

Figure 11:
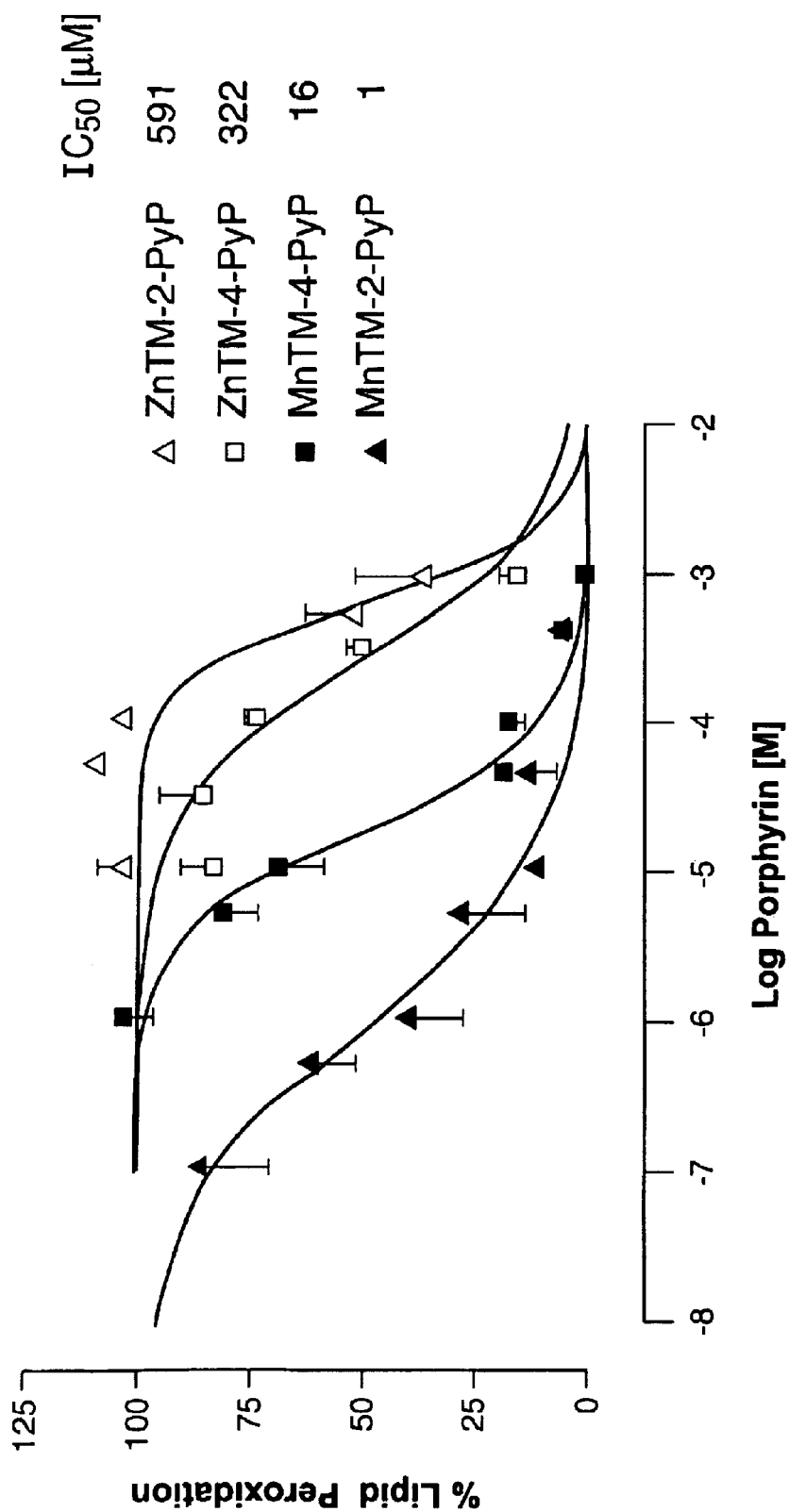

FIG. 11. The comparison of manganic (solid) and zinc (open) analogs of TM-4-PyP (squares) and TM-2-PyP (triangles) in their ability to inhibit iron/ascorbate mediated oxidation of rat brain homogenates. Rat brain homogenates were incubated for 30 minutes with 0.25 $\mu$M $FeCl_2$ and 1 $\mu$M ascorbate, and lipid peroxidation was measured as thiobarbituric acid reactive species. The amount of TBARS formed in 30 minutes was expressed as 100% lipid peroxidation (n=3–6). Sigmoidal dose response curves were derived from fitting the data to a non-linear regression program.

DETAILED DESCRIPTION OF THE INVENTION

The present invention relates to methods of protecting against the deleterious effects of oxidants, particularly, superoxide radicals, hydrogen peroxide and peroxynitrite, and to methods of preventing and treating diseases and disorders that involve or result from oxidant stress. The invention also relates methods of modulating biological processes involving oxidants, including superoxide radicals, hydrogen peroxide, nitric oxide and peroxynitrite. The invention further relates to compounds and compositions, including low molecular weight antioxidants (eg mimetics of scavengers of reactive oxygen species, including mimetics of SODs, catalases and peroxidases) and formulations thereof, suitable for use in such methods.

Mimetics of scavengers of reactive oxygen species appropriate for use in the present methods include methine (ie meso) substituted porphines, or pharmaceutically acceptable salts thereof. The invention includes both metal-free and metal-bound porphines. In the case of metal-bound porphines, manganic derivatives of methane (meso) substituted porphines are preferred, however, metals other than manganese, such as iron (II or III), copper (I or II), cobalt (II or III), or nickel (I or II), can also be used. It will be appreciated that the metal selected can have various valence states, for example, manganese II, III or V can be used. Zinc (II) can also be used even though it does not undergo a valence change and therefore will not directly scavenge superoxide. The choice of the metal can affect selectivity of the oxygen species that is scavenged. Iron-bound porphines, for example, can be used to scavenge NO· while manganese-bound porphines cannot. These metal bound porphines scavenge peroxynitrite; iron, nickel and cobalt bound porphines tend to have the highest reactivity with peroxynitrite.

Preferred mimetics of the invention are of Formula I or II:

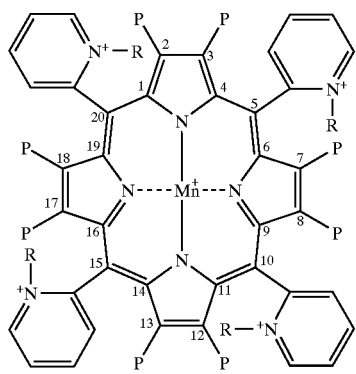

Formula I

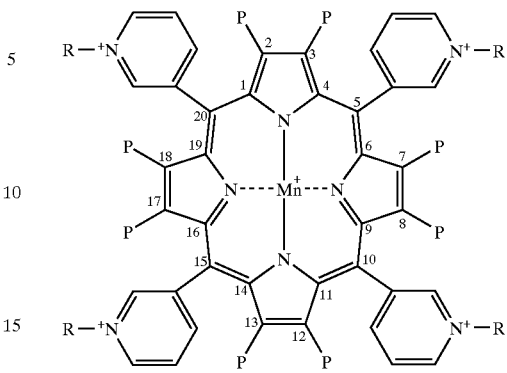

Formula II or pharmaceutically acceptable salt thereof, wherein R is $C_1$–$C_8$ alkyl, preferably, $C_1$–$C_4$ alkyl, more preferably, methyl, ethyl or isopropyl, most preferably methyl. This mimetic can also be present metal-free or bound to a metal other than Mn. All atropoisomers of the above are within the scope of the invention, present in isolated form or as a mixture of at least two. Atropoisomers wherein at least 3, preferably 4, of the R groups are above the porphyrin ring plane can be particularly advantageous.

One or more of the pyrrole rings of the porphyrin of Formula I or II can be substituted at any or all beta carbons, ie: 2, 3, 7, 8, 12, 13, 17 or 18. Such substituents, designated P, can be an electron withdrawing group, for example, each P can, independently, be a $NO_2$ group, a halogen (eg Cl, Br or F), a nitrile, a vinyl group, or a formyl group. For example, there can be 1, 2, 3, 4, 5, 6, 7 or 8 halogen (eg Br) substituents (when there are less than 8 halogen substituents, the remaining P's are advantageously hydrogen). Such substituents alter the redox potential of the porphyrin and thus enhance its ability to scavenge oxygen radicals. Each P can, independently, also be hydrogen. When P is formyl, it is preferred that there be not more than 2 (on non adjacent carbons), more preferably 1, the remaining P's being hydrogen. When P is $NO_2$, it is preferred that there be not more than 4 (on non adjacent carbons), more preferably 1 or 2, the remaining P's being hydrogen.

Mimetics suitable for use in the present methods can be selected by assaying for SOD, catalase and/or peroxidase activity and stability. Mimetics can also be screened for their ability to inhibit lipid peroxidation in tissue homogenates using iron and ascorbate to initiate the lipid peroxidation and measuring the formation of thiobarbituric acid reactive species (TBARS) (Ohkawa et al, Anal. Biochem. 95:351 (1979) and Yue et al, J. Pharmacol. Exp. Ther. 263:92 (1992)). The selective, reversible and SOD-sensitive inactivation of aconitase by known $O^-_2$ generators can be used as a marker of intracellular $O^-_2$ generation. Thus, suitable mimetics can be selected by assaying for the ability to protect aconitase activity.

SOD activity can be monitored in the presence and absence of EDTA using the method of McCord and Fridovich (J. Biol. Chem. 244:6049 (1969)). The efficacy of a mimetic can also be determined by measuring the effect of the mimetic on the aerobic growth of a SOD null E. coli strain versus a parental strain lacking the specific mutations. Specifically, parental E. coli (AB1157) and SOD null E. coli. (JI132) can be grown in M9 medium containing 0.2% casamino acids and 0.2% glucose at pH 7.0 and 37° C.; growth can be monitored in terms of turbidity followed at 700 nm. This assay can be made more selective for SOD mimetics by omitting the branched chain, aromatic and sulphur containing amino acids from the medium (glucose minimal medium (M9), plus 5 essential amino acids) (see Example V).

Efficacy of active mimetics can also be assessed by determining their ability to protect mammalian cells against methylviologen (paraquat)-induced toxicity Specifically, rat L2 cells grown as described below and seeded into 24 well dishes can be pre-incubated with various concentrations of the SOD mimetic and then incubated with a concentration of methylviologen previously shown to produce an $LC_{75}$ in control L2 cells. Efficacy of the mimetic can be correlated with a decrease in the methylviologen-induced LDH release (St. Clair et al, FEBS Lett. 293:199 (1991)).

The efficacy of SOD mimetics can be tested in vivo with mouse and/or rat models using both aerosol administration and parenteral injection. For example, male Balb/c mice can be randomized into 4 groups of 8 mice each to form a standard 2×2 contingency statistical model. Animals can be treated with either paraquat (40 mg/kg, ip) or saline and treated with SOD mimetic or vehicle control. Lung injury can be assessed 48 hours after paraquat treatment by analysis of bronchoalveolar lavage fluid (BALF) damage parameters (LDH, protein and % PMN) as previously described (Hampson et al, Tox. Appl. Pharm. 98:206 (1989); Day et al, J. Pharm. Methods 24:1 (1990)). Lungs from 2 mice of each group can be instillation-fixed with 4% paraformaldehyde and processed for histopathology at the light microscopic level.

Catalase activity can be monitored by measuring absorbance at 240 nm in the presence of hydrogen peroxide (see Beers and Sizer, J. Biol. Chem. 195:133 (1952)) or by measuring oxygen evolution with a Clark oxygen electrode (Del Rio et al, Anal. Biochem. 80:409 (1977)). Peroxidase activity can be measured spectrophotometrically as previously described by Putter and Becker: Peroxidases. In: Methods of Enzymatic Analysis, H. U. Bergmeyer (ed.), Verlag Chemie, Weinheim, pp. 286–292 (1983). Aconitase activity can be measured as described by Gardner and Fridovich (J. Biol. Chem. 266:19328 (1991)). The ability of mimetics to inhibit lipid peroxidation is assessed as described by Ohkawa et al (Anal. Biochem. 95:351 (1979)) and Yue et al (J. Pharmacol. Exp. Ther. 263:92 (1992)).

Active mimetics can be tested for toxicity in mammalian cell culture by measuring lactate dehydrogenase (LDH) release. Specifically, rat L2 cells (a lung Type II like cell; (Kaighn and Douglas, J. Cell Biol. 59:160a (1973)) can be grown in Ham's F-12 medium with 10% fetal calf serum supplement at pH 7.4 and 37° C.; cells can be seeded at equal densities in 24 well culture dishes and grown to approximately 90% confluence; SOD mimetics can be added to the cells at log doses (eg micromolar doses in minimal essential medium (MEM)) and incubated for 24 hours. Toxicity can be assessed by morphology and by measuring the release of the cytosolic injury marker, LDH (eg on a thermokinetic plate reader), as described by Vassault (In: Methods of Enzymatic Analysis, Bergmeyer (ed) pp. 118–26 (1983); oxidation of NADH is measured at 340 nm).

Synthesis of mimetics suitable for use in the present method can be effected using art-recognized protocols (see also Examples I, II, III and IV and Sastry et al, Anal. Chem. 41:857 (1969), Pasternack et al, Biochem. 22:2406 (1983); Richards et al, Inorg. Chem. 35:1940 (1996) and U.S. application Ser. No. 08/663,028, particularly the details therein relating to syntheses). Separation of atropoisomers can be effected using a variety of techniques.

One specific embodiment of the present invention relates to a method of regulating NO· levels by targeting the above-described porphines to strategic locations. NO· is an intercellular signal and, as such, NO· must traverse the extracellular matrix to exert its effects. NO·, however, is highly sensitive to inactivation mediated by $O_2^-$ present in the extracellular spaces. The methine (meso) substituted porphyrins of the invention can increase bioavalability of NO· by preventing its degradation by $O_2^-$.

In a further embodiment, the mimetics of the invention are used as catalytic scavengers of reactive oxygen species to protect against ischemia reperfusion injuries associated with myocardial infarction, stroke, acute head trauma, organ reperfusion following transplantation, bowel ischemia, hemorrhagic shock, pulmonary infarction, surgical occlusion of blood flow, and soft tissue injury. The mimetics can further be used to protect against skeletal muscle reperfusion injuries. The mimetics can also be used to protect against damage to the eye due to sunlight (and to the skin) as well as glaucoma, and macular degeneration in the eye. The mimetics can also be used to protect against and/or treat cataracts. The mimetics can also be used to protect against and/or treat inflammatory diseases of the skin (e.g., psoriasis). Diseases of the bone are also amenable to treatment with the mimetics. Further, connective tissue disorders associated with defects in collagen synthesis or degradation can be expected to be susceptible to treatment with the present mimetics, as should the generalized deficits of aging.

In yet another embodiment, the mimetics of the invention can be used as catalytic scavengers of reactive oxygen species to increase the very limited storage viability of transplanted hearts, kidneys, skin and other organs and tissues. The invention also provides methods of inhibiting damage due to autoxidation of substances resulting in the formation of $O_2^-$ including food products, pharmaceuticals, stored blood, etc. To effect this end, the mimetics of the invention are added to food products, pharmaceuticals, stored blood and the like, in an amount sufficient to inhibit or prevent oxidation damage and thereby to inhibit or prevent the degradation associated with the autoxidation reactions. (For other uses of the mimetics of the invention, see U.S. Pat. No. 5,227,405). The amount of mimetic to be used in a particular treatment or to be associated with a particular substance can be determined by one skilled in the art.

In yet another embodiment, the mimetics of the invention can be used to scavenge hydrogen peroxide and thus protect against formation of the highly reactive hydroxyl radical by interfering with Fenton chemistry (Aruoma and Halliwell, Biochem. J. 241:273 (1987); Mello Filho et al, Biochem. J. 218:273 (1984); Rush and Bielski, J. Phys. Chem. 89:5062 (1985)). The mimetics of the invention may also be used to scavenge peroxynitrite, as demonstrated indirectly by inhibition of the oxidation of dihydrorhodamine 123 to rhodamine 123 and directly by accelerating peroxynitrite degradation by stop flow analysis.

Further examples of specific diseases/disorders appropriate for treatment using the mimetics of the present invention include diseases of the central nervous system (including AIDS dementia, stroke, amyotrophic lateral sclerosis (ALS), Parkinson's disease and Huntington's disease) and diseases of the musculature (including diaphramic diseases (eg respiratory fatigue in emphysema, bronchitis and cystic fibrosis), cardiac fatigue of congestive heart failure, muscle weakness syndromes associated with myopathies, ALS and multiple sclerosis). Many neurologic disorders (including stroke, Huntington's disease, Parkinson's disease, ALS, Alzheimer's and AIDS dementia) are associated with an over stimulation of the major subtype of glutamate receptor, the NMDA (or N-methyl-D-aspartate) subtype. On stimulation of the NMDA receptor, excessive neuronal calcium concentrations contribute to a series of membrane and cytoplasmic events leading to production of oxygen free radicals and nitric oxide (NO·). Interactions between oxygen free radicals and NO· have been shown to contribute to neuronal cell death. Well-established neuronal cortical culture models of NMDA-toxicity have been developed and used as the basis for drug development. In these same systems, the mimetics of the present invention inhibit NMDA-induced injury. The formation of $O^-_2$ radicals is an obligate step in the intracellular events culminating in excitotoxic death of cortical neurons and further demonstrate that the mimetics of the invention can be used to scavenge $O^-_2$ radicals and thereby serve as protectants against excitotoxic injury.

The present invention also relates to methods of treating AIDS. The NfKappa B promoter is used by the HIV virus for replication. This promoter is redox sensitive, therefore, an antioxidant can regulate this process. This has been previously shown for two metalloporphyrins distinct from those of the present invention (Song et al, Antiviral Chem. And Chemother. 8:85 (1997)). The invention also relates to methods of treating arthritis, systemic hypertension, atherosclerosis, edema, septic shock, pulmonary hypertension, including primary pulmonary hypertension, impotence, MED, infertility, endometriosis, premature uterine contractions, microbial infections, gout and in the treatment of Type I and Type II diabetes mellitus. The mimetics of the invention can be used to ameliorate the toxic effects associated with endotoxin, for example, by preserving vascular tone and preventing multi-organ system damage.

Inflammations, particularly inflammations of the lung, are amenable to treatment using the present invention (note particularly the inflammatory based disorders of asthma, ARDS including oxygen toxicity, pneumonia (especially AIDS-related pneumonia), cystic fibrosis, chronic sinusitis and autoimmune diseases (such as rheumatoid arthritis)). EC-SOD is localized in the interstitial spaces surrounding airways and vasculature smooth muscle cells. EC-SOD and $O_2^-$ mediate the antiinflammatory-proinflammatory balance in the alveolar septum. NO· released by alveolar septal cells acts to suppress inflammation unless it reacts with $O_2^-$ to form ONOO$^-$. By scavenging $O_2^-$, EC-SOD tips the balance in the alveolar septum against inflammation. Significant amounts of ONOO$^-$ will form only when EC-SOD is deficient or when there is greatly increased $O_2^-$ release. Mimetics described herein can be used to protect against destruction caused by hyperoxia.

The invention further relates to methods of treating memory disorders. It is believed that nitric oxide is a neurotransmitter involved in long-term memory potentiation. Using an EC-SOD knocked-out mouse model (Carlsson et al, Proc. Natl. Acad. Sci. USA 92:6264 (1995)), it can be shown that learning impairment correlates with reduced superoxide scavenging in extracellular spaces of the brain. Reduced scavenging results in higher extracellular $O^-_2$ levels. $O^-_2$ is believed to react with nitric oxide thereby preventing or inhibiting nitric oxide-medicated neurotransmission and thus long-term memory potentiation. The mimetics of the invention can be used to treat dementias and memory/learning disorders.

The availability of the mimetics of the invention also makes possible studies of processes mediated by $O_2^-$, hydrogen peroxide, nitric oxide and peroxynitrite.

The mimetics described above can be formulated into pharmaceutical compositions suitable for use in the present methods. Such compositions include the active agent (mimetic) together with a pharmaceutically acceptable carrier, excipient or diluent. The composition can be present in dosage unit form for example, tablets, capsules or suppositories. The composition can also be in the form of a sterile solution suitable for injection or nebulization. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought.

The dosage of the composition of the invention to be administered can be determined without undue experimentation and will be dependent upon various factors including the nature of the active agent, the route of administration, the patient, and the result sought to be achieved. A suitable dosage of mimetic to be administered, for example, IV or topically, can be expected to be in the range of about 0.01 to 100 mg/kg/day, preferably 0.1 to 10 mg/kg/day. For aerosol administration, it is expected that doses will be in the range of 0.01 to 1.0 mg/kg/day. Suitable doses of mimetics will vary, for example, with the mimetic and with the result sought. The results of Faulkner et al (J. Biol. Chem. 269:23471 (1994)) indicate that the in vivo oxidoreductase activity of the mimetics is such that a pharmaceutically effective dose will be low enough to avoid problems of toxicity. Doses that can be used include those in the range of 1 to 50 mg/kg.

Certain aspects of the present invention will be described in greater detail in the non-limiting Examples that follow.

EXAMPLES

The following chemicals were utilized in Examples I–V that follow.

The chloride salts of ortho and meta metal-free ligands ($H_2TM$-2-PyPCl$_5$ and $H_2TM$-3-PyPCl$_5$) were purchased from MidCentury Chemicals, and the tosylate salts of the para metal-free ligand $H_2TM$-4-PyP(CH$_5$PhSO$_3$)$_5$) were purchased from Porphyrin Products. The purity was checked in terms of elemental analysis and spectral properties, ie, molar absorptivities and corresponding wave-length of the Soret bands. The Soret band properties of metal-free ligands were $\epsilon_{413.3\ nm}=2.16\times10^5 M^{-1}cm^{-1}$ ($H_2TM$-2-PyPCl$_4$), $\epsilon_{416.6\ nm}=3.18\times10^5\ M^{-1}cm^{-1}$ ($H_2TM$-3-PyPCl$_4$), $\epsilon_{422.0\ nm}=2.35\times10^5\ M^{-1}cm^{-1}$ ($H_2TM$-4-PyPCl$_4$). The non-methylated ortho metal-free ligand ($H_2T$-2-PyP) was bought from MidCentury Chemicals and the purity checked in terms of elemental analysis (see below). Iodoethane, 1-iodobutane, anhydrous manganese chloride (MnCl$_2$), MnCl$_2$.4H$_2$O, tetrabutylammonium chloride (TBA) and ammonium hexafluorophosphate (PF$_6$NH$_4$) were purchased from Aldrich.

Example I

Synthesis of meso-tetrakis-(N-methylpyridinium-2-yl)porphyrin and meso-tetrakis-(N-methylpyridinium-3-yl)porphyrin Metal-free porphyrins meso-tetrakis-(2-pyridyl)porphyrin ($H_2T$-2-PyP) and meso-tetrakis-(3-pyridyl)porphyrin ($H_2T$-3-PyP) were synthesized via Rothmund condensation with use of a modified Adler procedure (Kalyanasundaram, Inorg. Chem. 23:2453 (1984); (Torrens et al, J. Am. Chem. Soc.

94:4160 (1972)). Into a 100 mL refluxing solution of propionic acid were slowly injected equimolar amounts of freshly distilled pyrrole and pyridine-2- or pyridine-3-carboxyladehyde, and the solution was allowed to reflux for about 45 min, after which the propionic acid was distilled off. The black residues were neutralized with NaOH, washed with methanol, dissolved in $CH_2Cl_2$ (dichloromethane) and chromotographed on a neutral Woelm alumina column prepared with acetone. After elution of a pale blue fraction, $H_2TPyP$ was eluted with the use of $CH_2Cl_2$ containing 5–10% of pyridine. Shiny dark purple crystals were recovered from the dark red eluant after removal of solvents on rotavaporator. Methylation of $H_2TPyPs$ was carried using the excess of methyl-p-toluensulfonate in refluxing chloroform (Kalyanasundaram, Inorg. Chem. 23:2453 (1984); (Hambright et al, Inorg. Chem. 15:2314 (1976)). Both of the alkylated porphyrins spontaneously precipitated from hot chloroform solutions and were washed with ether and air dried.

Example II

Preparation of Manganese Complexes of Ortho, Meta and Para Isomers of $H_2TMPyP^{4+}$ The metallation was performed in water at room temperature. The porphyrin to metal ratio was 1:5 in the case of meta and ortho isomers and 1:14 in the case of para isomer. The solid $MnCl_2 \times 4\ H_2O$ (Aldrich) was added to the aqueous metal-free porphyrins after the pH of the solution was brought to ~pH=10.2. The metallation was completed inside an hour in the cases of all three isomers. For the preparation of ortho and meta compounds, $MnTM-2-PyP^{5+}$ and $MnTM-3-PyP^{5+}$, 300 mg of the metal-free ligand, either $H_2TM-2-PyP^{4+}$ or $H_2TM-3-PyP^{4+}$, was dissolved in 100 mL water, pH brought to 10.2 with several drops of 1M NaOH, followed by the addition of 340 mg of $MnCl_2$. The metallation was followed spectrally through the disappearance of the Soret band of $H_2TM-2-PyP^{4+}$ or $H_2TM-3-PyP^{4+}$ at 413.3 nm or 416.6 nm, respectively, and the appearance of the Soret bands of manganese complexes at 454.1 nm and 459.8 nm, respectively.

The excess of metal was eliminated as follows for all three (ortho, meta and para) isomers of $MnTMPyP^{5+}$. The $MnTMPyP^{5+}$ was precipitated as $PF_6^-$ salt by adding 50-fold excess of $NH_4PF_6$. The precipitate was washed with 2-propanol:diethylether=1:1, and dried in vacuum at room temperature. Dry $PF_6^-$ salt of $MnTMPyP^{5+}$ was then dissolved in acetone (370 mg in 100 mL acetone) and 1 g of tetrabutylammonium chloride added. The precipitate was washed with acetone and dried overnight in vacuum at room temperature. In order to obtain a pure compound, the procedure was repeated. The elemental analysis was done for all metallated isomers. The compounds were analyzed in spectral terms and the following data were obtained: Soret bands properties of metallated compounds were: $\epsilon_{454.1\ nm}=12.3\times 10^4$ cm$^{-1}$ M$^{-1}$ (MnTM-2-PyPCl$_5$), $\epsilon_{459.8\ nm}=13.3\times 10^4$ cm$^{-1}$ M$^{-1}$ (MnTM-3-PyPCl$_5$), $\epsilon_{462.2\ nm}=13.9\times 10^4$ cm$^{-1}$ M$^{-1}$ (MnTM-4-PyPCl$_5$).

Metallation was performed in methanol as well. In addition, when performed in water, the metal:ligand ratio varied from 1:5, to 1:14 to 1:100. Under all conditions, the given molar absorptivities were obtained. The calculations were based on the metal-free ligands that were analyzed prior to metallation. The molar absorptivities of the metal-free ligands were consistent with literature as well as their elemental analyses.

The elemental analyses of MnTM2-PyPCl$_5$ and MnTM-3-PyPCl$_5$ are shown in Table 1.

TABLE 1

|  | C* | H* | N* |
|---|---|---|---|
| MnTM2-PyPCl$_5$.6 H$_2$O | 52.99 (52.90) | 4.85 (4.64) | 11.22 (11.21) |
| MnTM-3-PyPCl$_5$.3 H$_2$O | 55.41 (54.87) | 4.97 (4.40) | 11.10 (11.69) |

*Found (calcd).

Example III

Synthesis of Manganic Meso-tetrakis-(N-ethylpyridinium-2-yl)porphyrin 50 mg of $H_2T-2-PyP$ was dissolved in 30 mL of anhydrous dimethylformamide (DMF) and the solution was stirred and heated at 100° C. 20 mg of anhydrous $MnCl_2$ (20 eq) were added and the solution stirred for 3 days. The completion of the metallation was checked by UV spectroscopy. Upon metallation, the temperature was decreased to 60° C., 0.65 mL of iodoethane (100 eq) was added, and the solution was stirred for 7 days (Perree-Fauvet et al, Tetrahedron 52:13569 (1996)). DMF was evaporated, 10 mL of acetone was added, and the product was precipitated adding 20 mL of a solution of TBA in acetone (0.45 M); indeed, contrary to the iodide salt, the chloride salt precipitates in acetone. The product was purified using the "double precipitation" method, as described above. The product was dried overnight in vacuum, over $P_2O_5$, at 70° C., leading to 125 mg (95%) of a dark purple solid. UV (H$_2$O), $\epsilon_{454.0\ nm}=1.41\times 10^5$ M$^{-1}$cm$^{-1}$. Elemental analysis, calcd. for MnC$_{48}$N$_8$H$_{44}$Cl$_5$.5H$_2$O: C, (54.64), H, (5.16), N, (10.62); found: C, (54.55), H, (5.36), N, (10.88).

Example IV

Synthesis of Manganic Meso-tetrakis-(N-butylpyridinium-2-yl)porphyrin

The same procedure described above was used. 0.92 mL of 1-iodobutane (100 eq) was added and the mixture stirred at 100° C. for 7 days. Drying of the chloride salt resulted in 70 mg (50%) of a dark purple viscous product. The elemental analysis was thus performed on the hexafluorophosphate salt (non-viscous) The chlorine salt is water-soluble (micelles were not observed). UV(H$_2$O) of the chloride salt, $\epsilon_{454.0}$ 1.21×10$^5$M$^{-1}$cm$^{-1}$. Elemental analysis, calcd. For MnC$_{56}$H$_{60}$N$_{8}P5$F$_{30}$.H$_2$O: C, (40.94), H, (3.80), N, (6.82); found: C, (41.15), H, (4.35), N, (6.52).

Example V

Figure 1:
FIG. 1. Mechanism.
Figure 1:
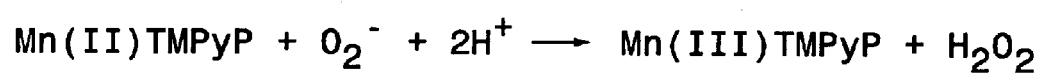
Figure 2:
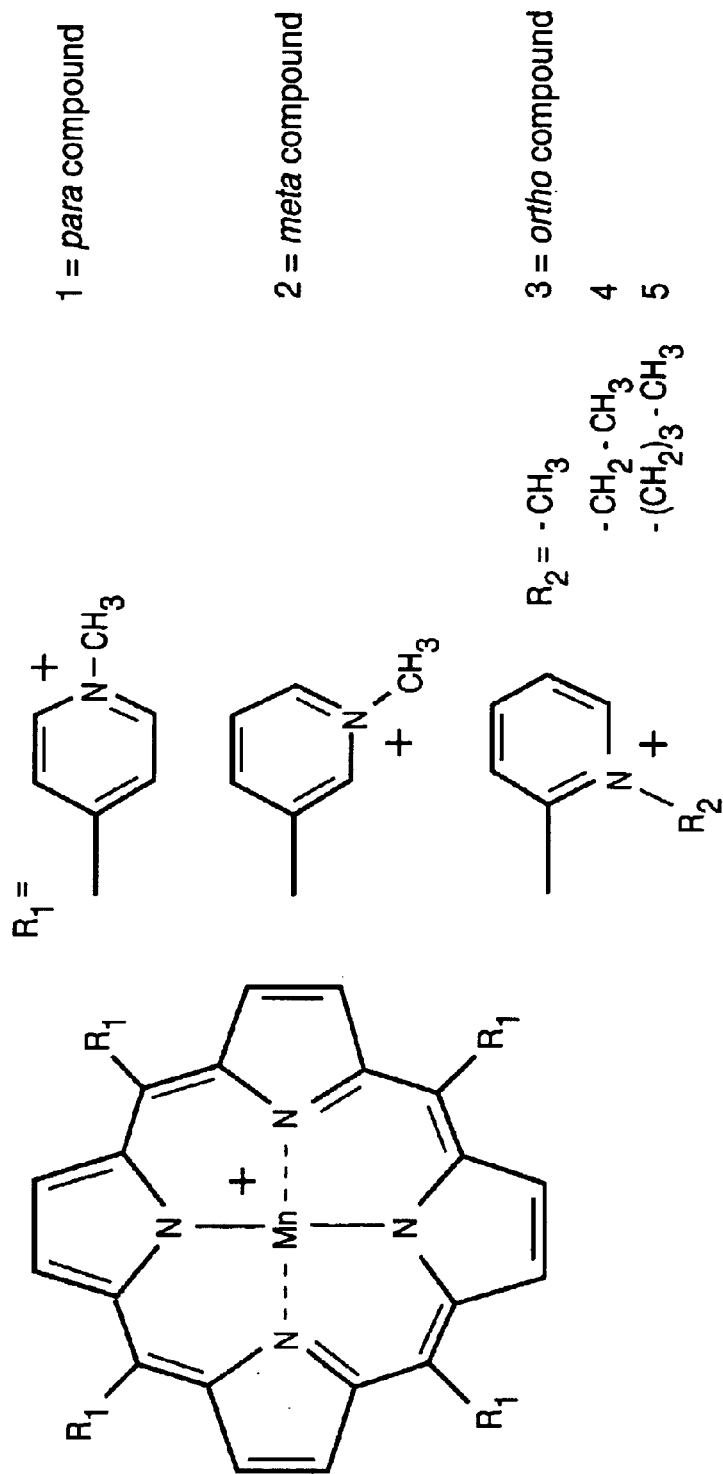
FIG. 2. Manganese meso-tetrakis-N-alkyl-pyridinium based porphyrins.

The Ortho Effect Makes Manganic Meso-tetrakis-(N-alkylpyridinium-2-yl)-porphyrin a Powerful Superoxide Dismutase Mimic The superoxide dismutase activity of the mimetics of the invention depends on a number of factors, including thermodynamic factors (eg the metal-centered redox-potential see FIG. 1)), and kinetic factors (eg electrostatic facilitation). In an in vitro enzymatic assay of SOD activity (see McCord and Fridovich, J. Biol. Chem. 244:6049 (1969)) the ortho compound "3" proves to be more than an order of magnitude more active than the para compound "1" (see FIG. 2 (note also Table 2 where "2" is the meta compound and "4" and "5" are ortho compounds that carry 4 ethyl or 4 butyl groups, respectively)).

Figure 3:
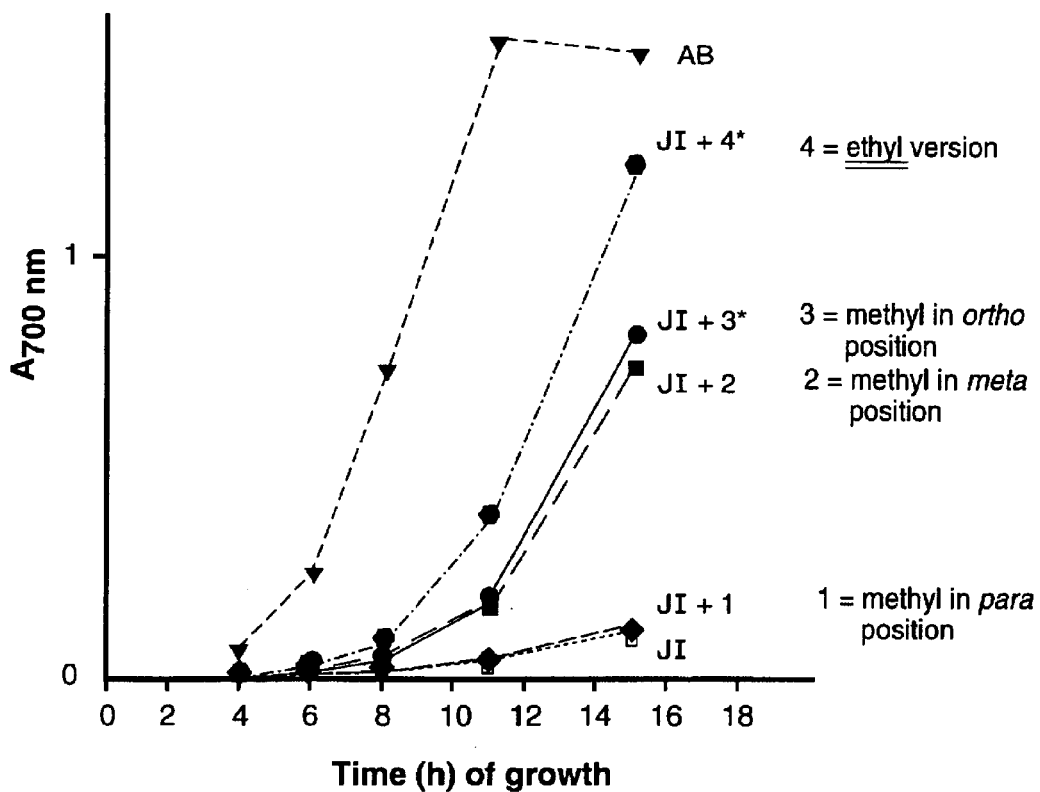
FIG. 3. SOD activity in vivo (*E. coli*) of 1, 2, 3* and 4* (20 μM) in minimal medium (mixture of atropoisomers, JI=SOD deficient strain, AB=parental strain).

The activity in vivo of the mimetics of the invention can be tested on an *E. coli* strain deleted of the genes coding for both the MnSOD and FeSOD. In this assay, the efficacy of a mimetic is determined by measuring the effect of the mimetic on the aerobic growth of a SOD null *E. coli* strain versus a parental strain. Specifically, parental *E. coli* (AB1157) and SOD null *E. coli*. (JI132) are grown in M9 medium containing 0.2% casamino acids and 0.2% glucose at pH 7.0 and 37° C.; growth is monitored in terms of turbidity followed at 700 nm. This assay is made more selective for SOD mimetics by omitting the branched chain, aromatic and sulphur containing amino acids from the medium (glucose minimal medium (M9), plus 5 essential amino acids). As shown in FIG. 3, the increase in activity by the "ortho effect" was confirmed in that, under these growth conditions, SOD null cells cultured in the presence of compound "1" did not show an increase in $A_{700}$ while such cells cultured in the presence of compounds "3" and "4" (as well as "2") did.

The "ortho effect" also decreases the toxicity. It is well known that porphyrins, and particularly cationic porphyrins, interact with DNA and can act as DNA cleavers. This fact can be an issue in the use of metallo-porphyrins as anti-tumor drugs. The present mimetics avoid this interaction. In addition to the increase in activity, the interaction with DNA of the meta "2" and the ortho "3" compounds, is greatly decreased. This is clearly demonstrated by the measurements of the SOD activity in vitro in the presence of DNA (see Table 2), and by the decreased toxicity in vivo (*E. coli*) (see FIG. 3).

In order to maximize the decrease in toxicity due to interaction with DNA, two derivatives of the ortho compound have been prepared which carry four ethyl or four butyl groups ("4" and "5", respectively). The ethyl derivative "4" was significantly less toxic than the methyl derivative "3" (see Table 2 and FIG. 3). However, in comparison to the ethylated derivative "4", the butylated derivative did not show a further decrease in toxicity (see Table 2). These data indicate that ortho ethyl groups are sufficient to inhibit binding of the porphyrin to DNA.

TABLE 2

| | $\delta_{SB}$ (nm) | $\epsilon(10^3)$ | $E_{½}$ (V) | $k_{cat}$ ($M^{-1}s^{-1}$) | DNA-$IC_{50}$ |
|---|---|---|---|---|---|
| 1 | 462.2 | 139 | +0.060 | 3.8 $10^6$ | 7.0 $10^{-6}$ |
| 2 | 459.8 | 133 | +0.042 | 4.1 $10^6$ | 2.2 $10^{-5}$ |
| 3* | 454.0 | 123 | | 4.5 $10^7$ | 3.3 $10^{-5}$ |
| 4* | 454.0 | 141 | | 4.5 $10^7$ | 6.7 $10^{-5}$ |
| 5* | 454.0 | 120 | | 3.0 $10^7$ | 6.7 $10^{-5}$ |

Table. UV parameters, redox potential (vs NHE), SOD like activity and DNA interaction parameters of 1, 2, 3 and its atropisomers, 4 and 5 (*mixture of atropisomers, $\delta_{SB}$ = Soret band wave-length, $\epsilon$ = molecular absortivity of the Soret band, $E_{½}$ = one-electron metal-centered redox-potential, $k_{cat}$ = rate constant for the superoxide dismutation reaction, DNA-$IC_{50}$ = concentration of DNA for 50% inhibition of the superoxide dismutation reaction).

Example VI

Syntheses and Superoxide Dismutating Activities of Partially (1 to 4) β-Chlorinated Derivatives of Manganese (III) Meso-tetrakis-(N-ethylpyridinium-2-yl)-Porphyrin Materials and Methods Materials. 5,19,15,20-Tetrakis-(2-pyridyl)-porphyrin ($H_2$T-2-PyP) was purchased from Mid-Century chemicals (Posen, Ill.) (Torrens et al, J. Am. Chem. Soc. 94:4160 (1972)). N-Chlorosuccinimide (NCS), ethyl-p-toluenesulfonate (ETS), tetrabutylammonium chloride (98%) (TBAC), ammonium hexafluorophosphate ($NH_4PF_6$), manganese chloride, sodium L-ascorbate (99%), cytochrome c, xanthine, ethylenedinitrilotetraacetic acid (EDTA), N,N,-dimethylformamide (98.8%, anhydrous) and 2-propanol (99.5%) were from Sigma-Aldrich. Ethanol (absolute), acetone, ethyl ether (anhydrous), chloroform and dichloromethane (HPLC grade) were from Mallinckrodt, and used without further purification. Xanthine oxidase was supplied by R. D. Wiley (Waud et al, Arch. Biochem. Biophys. 19:695 (1975)). Thin-layer chromatography (TLC) plates (Baker-flex silica gel IB) were from J. T. Baker (Phillipsburg, N.J.). Wakogel C-300 was from Wako Pure Industry Chemicals, Inc (Richmond, Va.).

Instrumentation. Proton nuclear magnetic resonance ($^1$H-NMR) spectra were recorded on a Varian Inova 400 spectrometer. Ultravisible/visible (UV/VIS) spectra were recorded on a Shimadzu spectrophotometer Model UV-260. Matrix-assisted laser desorption/ionization-time of flight—(MALDI-TOFMS) and electrospray/ionization (ESMS) mass spectrometry were performed on a Bruker Proflex III™ and a Fisons Instruments VG Bio-Q triple quadrupole spectrometers, respectively.

$H_2Cl_1$T-2-PyP. 50 mg ($8.1 \times 10^{-5}$ moles) of $H_2$T-2-PyP was refluxed in chloroform with 43 mg ($3.22 \times 10^{-4}$ moles) of NCS (Ochsenbein et al, Angew. Chem. Int. Ed. Engl. 33:348 (1994). The reaction was followed by normal phase silica TLC using a mixture EtOH/$CH_2Cl_2$ (5:95) as eluant. After 6 hours of reaction the solution was washed once with distilled water. The chloroform was evaporated and the products of the reaction were chromatographed over 100 g of Wakogel C-300 on a 2.5×50 cm column using the same eluant. The fraction corresponding to $H_2Cl_1$T-2-PyP was purified again using the same system leading to 16 mg of a black purple solid (30%). TLC: $R_f$=0.47. UV/VIS ($CHCl_3$): $\lambda_{nm}$ (log $\epsilon$) 419.6 (5.44), 515.2 (4.21), 590.0 (3.72), 645.8 (3.25). MALDI-TOFMS: m/z=654 (M+H$^+$). $^1$H-NMR ($CDCl_3$): $\delta_{ppm}$ −2.91 (2H, NH); 7.66–7.74 (m, 4H); 7.99–8.21 (m, 8H); 7.68 (s, 1H); 8.74 (d, 1H, J 6 Hz); 8.76 (d, 1H, J 6 Hz); 8.76 (d, 1H, J 6 Hz); 8.88 (d, 1H, J 6 Hz); 8.90 (d, 1H, J 6 Hz); 8.94 (d, 1H, J 6 Hz); 9.04–9.14 (m, 4H).

$H_2Cl_{2a}$T-2-PyP. The same procedure as described above, leading to 5.3 mg of a black purple solid (10%). TLC: $R_f$=0.50. UV/VIS ($CHCl_3$): $\lambda_{nm}$ (log $\epsilon$) 421.4 (5.38), 517.8 (4.21), 591.4 (3.78), 647.6 (3.51). MALDI-TOFMS: m/z= 688 (M+H$^+$). $^1$H-NMR ($CDCl_3$): $\delta_{ppm}$ −2.98 (2H, NH); 7.66–7.74 (m, 4H); 8.00–8.20 (m, 8H); 8.70 (s, 2H); 8.82 (d, 2H, J 6 Hz); 8.91 (d, 2H, J 6 Hz); 9.06–9.14 (m, 4H).

$H_2Cl_{2b+2c}$T-2-PyP. The same procedure leading to 11 mg of a black purple solid (20%). TLC: $R_f$=0.53. UV/VIS ($CHCl_3$): $\lambda_{nm}$ (log $\epsilon$) 421.4 (5.42), 516.8 (4.25), 593.2 (3.74), 646.2 (3.31); MALDI-TOFMS, m/z=688 (M+H$^+$). $^1$H-NMR ($CDCl_3$): $\delta_{ppm}$ −3.04 (2H, NH); −2.84 (1H, NH); −2.87 (1H, NH); 7.66–7.74 (m, 8H); 7.98–8.20 (m, 16H); 8.59 (s, 1H); 8.61 (s, 1H); 8.73 (d, 2H, J<2 Hz); 8.78 (d, 2H, J 6 Hz); 8.87 (d, 2H, J 6 Hz); 8.93 (d 2H, J<2 Hz); 9.02–9.14 (m, 8H).

$H_2Cl_3$T-2-PyP. The same procedure using 65 mg ($4.87 \times 10^{-4}$ moles) of NCS, leading to 8.4 mg of a black purple solid (14%). TLC: $R_f$=0.55. UV/VIS ($CHCl_3$): $\lambda_{nm}$ (log $\epsilon$) 422.8 (5.37), 519.4 (4.21), 593.8 (3.71), 651.4 (3.37). MALDI-TOFMS: m/z=723 (M+H$^+$). $^1$H-NMR ($CDCl_3$): $\delta_{ppm}$ −3.08 (1H, NH); −3.15 (1H, NH); 7.66–7.74 (m, 4H); 8.00–8.18 (m, 8H); 8.56 (s, 1H), 8.72 (d, 1H, J 6 Hz); 8.76 (d, 1H, J 6 Hz); 8.82 (d, 1H, J 6 Hz); 8.88 (d, 1H, J 6 Hz); 9.04–9.14 (m, 4H).

$H_2Cl_4$T-2-PyP. The same procedure using 65 mg ($4.87 \times 10^{-4}$ moles) of NCS, leading to 7.3 mg of a black purple solid (12%). TLC: $R_f$=0.58. UV/VIS ($CHCl_3$): $\lambda_{nm}$ (log $\epsilon$)

423.4 (5.33), 520.0 (4.19), 595.6 (3.66), 651.0 (3.33). MALDI-TOFMS m/z=758 (M+H$^+$). $^1$H-NMR (CDCl$_3$): $\delta_{ppm}$ −3.14 (2H, NH); 7.66–7.74 (m, 4H); 7.98–8.16 (m, 8H); 8.74 (d, 4H, J<2 Hz); 9.06–9.12 (m, 4H).

Figure 4:
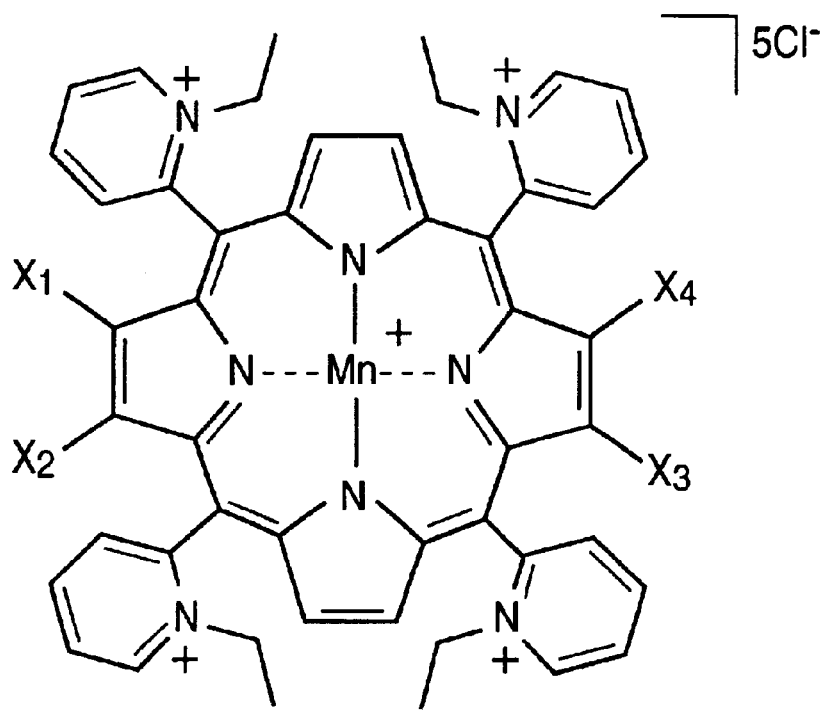
FIG. 4. Structures of $MnCl_xTE\text{-}2\text{-}PyP^{5+}$ (x=1 to 4).

MnTE-2-PyP$^{5+}$. 100 mg (1.62×10$^{-4}$ moles) of H$_2$T-2-PyP was dissolved in 5 mL of warm DMF (anhydrous), 5.5 mL (3.22×10$^{-2}$ moles) of ethyl-p-toluenesulfonate (ETS) was added under stirring at 90° C. and allowed to react for 24–48 hours. The completion of tetra-N-ethylation was followed by normal phase silica TLC using a mixture KNO$_{3sat}$/H$_2$O/CH$_3$CN (1:1:8) as eluant (Batinic-Haberle et al, J. Biol. Chem. 273:24521 (1998)). Upon the completion of the reaction, the DMF was removed in vacuo and 5 mL of acetone was then added. To this solution, a concentrated solution of tetrabutylammonium chloride (TBAC) in acetone (~1 g/10 mL acetone) was added dropwise under stirring until precipitation of the chloride was complete. The resulting purple solid was dissolved in 10 mL of water, the pH of the solution was raised to 12 with NaOH and 640 mg of MnCl$_2$4H$_2$O (3.23×10$^{-3}$ moles) was added (Batinic-Haberle et al, J. Biol. Chem. 273:24521 (1998). Upon completion of metallation, the pH was lowered between 4 and 7 in order to facilitate the auto-oxidation of Mn(II) into Mn(III), and the excess of metal was eliminated as follows. The solution was filtered, and a concentrated aqueous solution of NH$_4$PF$_6$ was added to precipitate the metalloporphyrin as the PF$_6^-$ salt (Batinic-Haberle et al, Arch. Biochem. Biophy. 343:225 (1997); Richards et al, Inorg. Chem. 35:1940 (1996)). The precipitate was thoroughly washed with a mixture 2-propanol/ethyl ether (1:1), dried in vacuo at room temperature. The resulting solid was then dissolved in acetone and a concentrated solution of TBAC was added to isolate the metalloporphyrin in the form of its chloride salt. The precipitate was washed thoroughly with acetone and dried in vacuo at room temperature leading to 150 mg of a black red solid (95%). TLC: R$_f$=0.18. UV/VIS (H$_2$O): $\lambda_{nm}$ (log $\epsilon$) 364.0 (4.64), 453.8 (5.14), 558.6 (4.05). ESMS: m/z=157.4 (M$^{5+}$/5). Anal. calcd. for MnC$_{48}$N$_8$H$_{44}$Cl$_5$.5H$_2$O: C, 54.64; H, 5.16; N, 10.62. Found: C, 54.55; H, 5.40; N, 10.39. (See FIG. 4 for compound structures).

MnCl$_1$TE-2-PyP$^{5+}$. The same procedure as described above starting from 10 mg (1.53×10$^{-5}$ moles) of H$_2$Cl$_1$T-2-PyP and 0.5 mL (2.94×10$^{-3}$ moles) of ETS in 1 mL of DMF. TLC: R$_f$=0.20. UV/VIS (H$_2$O): $\lambda_{nm}$ (log $\epsilon$) 365.6 (4.63), 455.6 (5.13), 560.6 (4.02). ESMS: m/z=164.3 (M$^{5+}$/5). Anal. calcd. for MnC$_{48}$N$_8$H$_{43}$Cl$_6$.5H$_2$O: C, 52.91; H, 4.90; N, 10.28. Found: C, 52.59; H, 5.28; N, 10.14.

MnCl$_{2a}$TE-2-PyP$^{5+}$. The same procedure starting from 5 mg (7.28×10$^{-6}$ moles) of H$_2$Cl$_{2a}$T-2-PyP and 0.25 ml (1.47×10$^{-3}$ moles) of ETS, leading to 7.5 mg of a black red solid (95%). TLC: R$_f$=0.21. UV/VIS (H$_2$O): $\lambda_{nm}$ (log $\epsilon$) 365.8 (4.58), 456.4 (5.05), 562.2 (4.00). ESMS: m/z=171.1 (M$^{5+}$/5). Anal. calcd. for MnC$_{48}$N$_8$H$_{42}$Cl$_7$.6H$_2$O: C, 50.48; H, 4.77; N, 9.81. Found: C, 50.08; H, 4.60; N, 10.01.

MnCl$_{2b+2c}$TE-2-PyP$^{5+}$. The same procedure starting from 5 mg (7.28×10$^{-6}$ moles) of H$_2$Cl$_{2b+2c}$T-2-PyP, leading to 7.5 mg of a black red solid (95%). TLC: R$_f$=0.22. UV/VIS (H$_2$O): $\lambda_{nm}$ (log $\epsilon$) 365.2 (4.63), 457.4 (5.08), 462.2 (4.06). ESMS: m/z=171.1 (M$^{5+}$/5). Anal. calcd. for MnC$_{48}$N$_8$H$_{42}$Cl$_7$.5H$_2$O: C, 51.29; H, 4.66; N, 9.97. Found: C, 51.31; H, 5.19; N, 9.68.

MnCl$_3$TE-2-PyP$^{5+}$. The same procedure starting from 5 mg (6.93×10$^{-6}$ moles) of H$_2$Cl$_3$T-2-PyP, leading to 7.5 mg of a black brown solid (95%). TLC: R$_f$=0.23. UV/VIS (H$_2$O): $\lambda_{nm}$ (log $\epsilon$) 364.8 (4.58), 458.0 (4.98), 466.4 (4.00). ESMS: m/z=178.1 (M$^{5+}$/5). Anal. calcd. for MnC$_{48}$N$_8$H$_{41}$Cl$_8$.6H$_2$O: C, 49.00; H, 4.54; N, 9.52. Found: C, 48.40; H, 4.26; N, 9.59.

MnCl$_4$TE-2-PyP$^{5+}$. The same procedure starting from 5 mg (6.61×10$^{-6}$ moles) of H$_2$Cl$_4$T-2-PyP, leading to 7.5 mg of a black brown solid (95%). TLC: R$_f$=0.24. UV/VIS (H$_2$O): $\lambda_{nm}$ (log $\epsilon$) 365.8 (4.52), 459.2 (4.90), 567.0 (3.96). ESMS: m/z=184.9 (M$^{5+}$/5). Anal. calcd. for MnC$_{48}$N$_8$H$_{40}$Cl$_9$.5H$_2$O: C. 48.33; H, 4.22; N, 9.39. Found: C, 48.38; H, 4.45; N, 9.53.

Electrochemistry. The electrochemical characterization was performed as described previously on a Voltammetric Analyzer Model 600 (CH instrument) using a glassy carbon electrode (Ag/AgCl reference and Pt auxiliary electrodes), at 0.5 mM porphyrin, pH 7.8 (0.05 M phosphate buffer), 0.1 M NaCl. The potentials were standardized against potassium ferricyanide/potassium ferrocyanide couple (Batinic-Haberle et al, Arch. Biochem. Biophys. 343:225 (1997); Kolthof et al, J. Phys. Chem. 39:945 (1974)).

Superoxide dismuting activity. The SOD-like activities were measured using the xanthine/xanthine oxidase system as a source of O$_2^-$ and ferricytochrome c as its indicating scavenger (McCord et al, J. Biol. Chem. 244:6049 (1969)). O$_2^-$ was produced at the rate of 1.2 $\mu$M per minute and reduction of ferricytochrome c was followed at 550 nm. Assays were conducted in presence of 0.1 mM EDTA in 0.05 M phosphate buffer (pH 7.8). Rate constants for the reaction of the compounds were based upon competition with 10 $\mu$M cytochrome c, k$_{cyt\ c}$=2.6×10$^5$ M$^{-1}$s$^{-1}$ (Butler et al, J. Biol. Chem. 257:10747 (1982)). All measurements were done at 25° C. Cytochrome c concentration was at least 10$^3$-fold higher than the concentrations of the SOD mimics and the rates were linear for at least two minutes, during which the compounds intercepted ~100 equivalents of O$_2^-$, thus confirming the catalytic nature of O$_2^-$ dismutation in presence of the mimics.

Results

Despite increasing knowledge on the purification of water soluble porphyrins, the separation of halogenated uncharged porphyrins followed by N-alkylation and metallation still appeared easier for the successful preparation of MnCl$_x$TE-2-PyP$^{5+}$ (Scheme A) (Richards et al, Inorg. Chem. 35:1940 (1996); Kaufman et al, Inorg. Chem. 34:5073 (1995)):

Scheme A

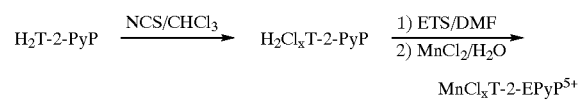

MnCl$_x$T-2-EPyP$^{5+}$

Synthesis of H$_2$T-2-PyP $\beta$-chlorinated derivatives. $\beta$-Chlorination of H$_2$T-2-PyP was performed as described in the literature for H$_2$TPP analogues, using N-chlorosuccinimide (NCS) in chloroform under refluxing conditions (Ochsenbein et al, Angew. Chem. Int. Ed. Engl. 33:348 (1994)). The number of NCS equivalents used can be 4 or 6, depending on the degree of substitution desired (Table 3). The reaction can be followed by TLC (silica gel) using a mixture ethanol/dichloromethane (5:95) as eluant (Table 3 and Scheme B).

TABLE 3

$H_2Cl_xT\text{-}2\text{-}PyP$ ($x$ = 1 to 4):
$R_f$, Soret band data and yields with 4 and 6 equivalents of NCS.

| Porphyrin | $R_f{}^a$ | $\lambda$nm ($\epsilon/10^5$ M$^{-1}$ cm$^{-1}$)$^b$ | Yield (%)$^c$ 4 eq | 6 eq |
|---|---|---|---|---|
| $H_2T\text{-}2\text{-}PyP$ | 0.43 | 418.4 | | |
| $\beta\text{-}Cl_1$ | 0.47 | 419.6 (2.74) | 30 | — |
| $\beta\text{-}Cl_{2a}$ | 0.50 | 421.4 (2.39) | 10 | 5 |
| $\beta\text{-}Cl_{2b-2c}$ | 0.53 | 421.4 (2.62) | 20 | 10 |
| $\beta\text{-}Cl_3$ | 0.55 | 422.8 (2.33) | 10 | 15 |
| $\beta\text{-}Cl_4$ | 0.58 | 423.6 (2.13) | 7 | 12 |

$^a$TLC on silica with EtOH/CH$_2$Cl$_2$ (5.95) as eluant.
$^b$in CHCl$_3$ (estimated errors for $\epsilon$ are within ±10%).
$^c$in refluxing CHCl$_3$ during 6 hours (c ~ 2 μM).

Scheme B

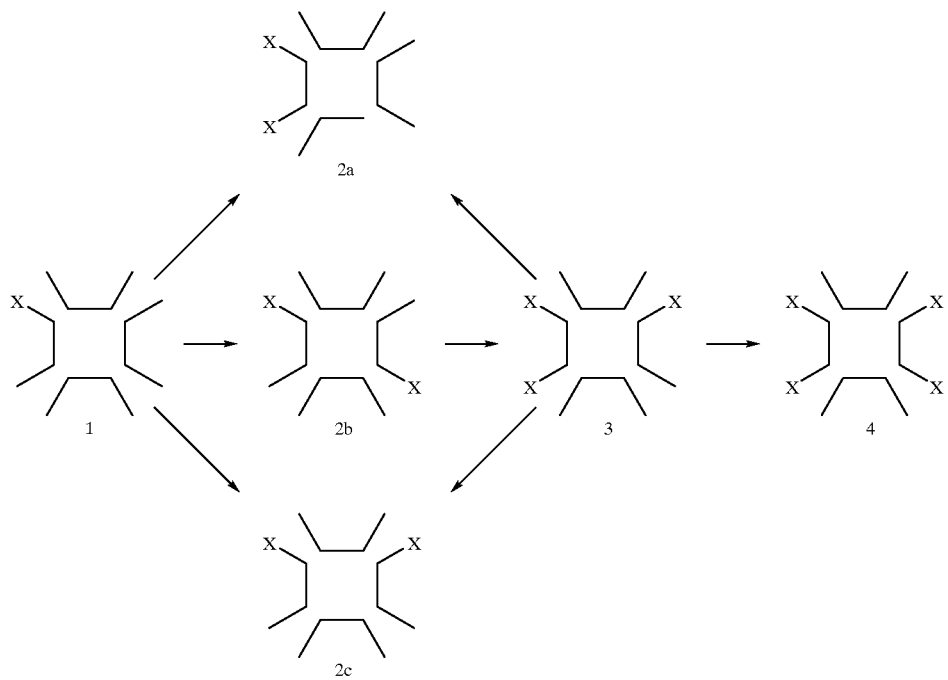

Each compound was purified by chromatography on silica gel (Wakogel C-300) using the same eluant. The structures of the main isomers were identified by mass spectrometry, and UV/VIS and $^1$H-NMR spectroscopies (Table 3 and Scheme B). The bathochromic shift of the Soret band per chlorine on H$_2$T-2-PyP was only 1.3 nm compared to 3.5 nm reported previously for H$_2$TPP derivatives (Table 3) (Hoffmann et al, Bull. Soc. Chem. Fr. 129:85 (1992); Chorghade et al, Synthesis 1320 (1996); Wijesekera et al, Bull. Chem. Fr. 133:765 (1996)). Only one of the three dichlorinated regioisomers ($\beta$-Cl$_{2a}$ derivative) was purified by chromatography on silica gel. Its two other regioisomers ($\beta$-Cl$_{2b}$ and $\beta$-Cl$_{2c}$ derivatives) exhibited the same $R_f$. Preliminary results showed that purification of H$_2$Br$_x$T-4-PyP (x=1 to 4) is more difficult. Indeed, using the same TLC system, $\beta$-Br$_1$ and $\beta$-Br$_{2a}$ derivatives both have the same $R_f$, and no difference of $R_f$ between $\beta$-Br$_{2b}$, $\beta$-Br$_{2c}$, $\beta$-Br$_3$ and $\beta$-Br$_4$ derivatives was observed, showing clearly that, in this case, $R_f$ depends on the number of pyrroles substituted and not on the number of $\beta$-protons substituted.

Figure 5:
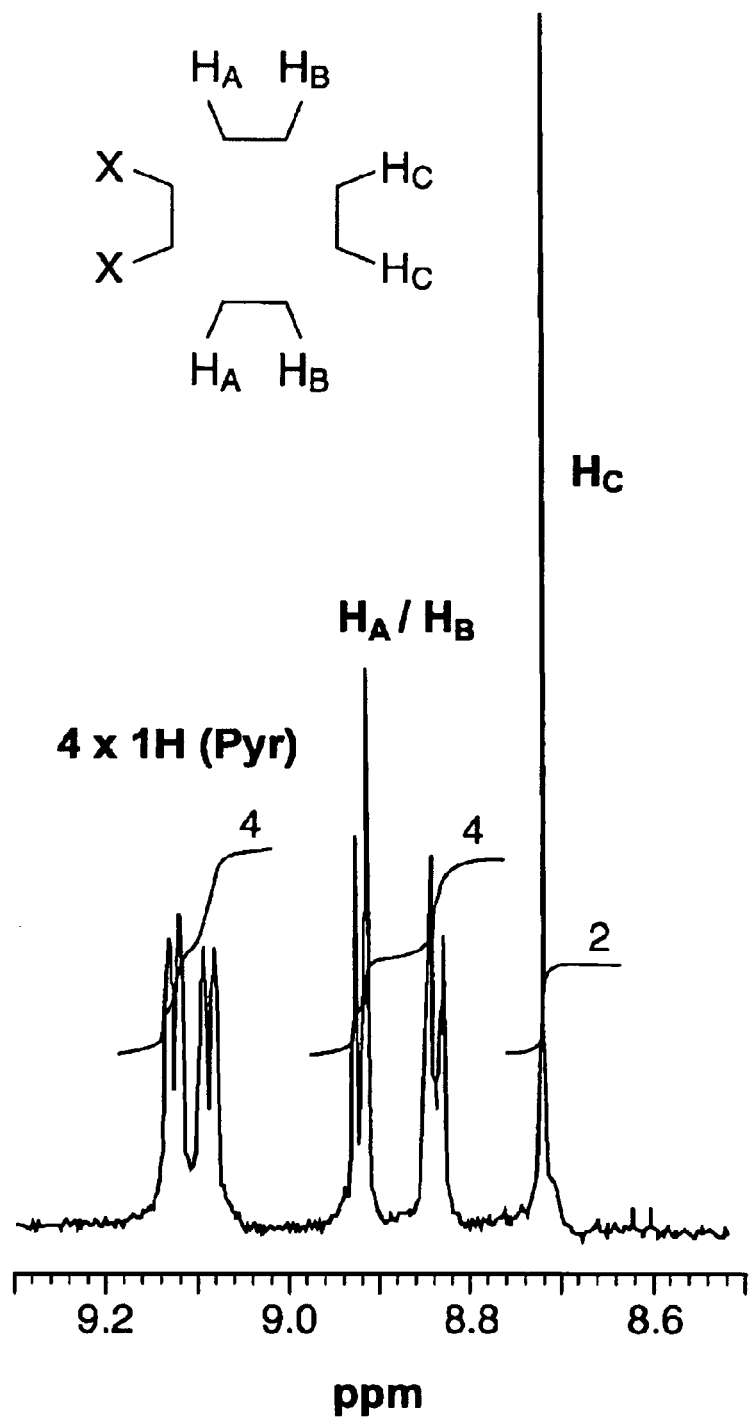
FIG. 5. $^1$H-NMR spectrum (porphyrin ring) of $H_2Cl_{2a}T$-2-PyP in $CDCl_3$ (δ=7.24 ppm). The four protons in alpha position of the four pyridyl nitrogens are taken as integration reference.

$^1$H-NMR identification of H$_2$T-2-PyP $\beta$-chlorinated derivatives. $^1$H-NMR allowed the identification of the products of the substitution reaction (Table 4 and FIG. 5). As described in the literature for H$_2$TPP analogues, the main regioisomer of H$_2$Cl$_4$T-2-PyP has chlorines in positions 7,8,17,18. Indeed, its $^1$H-NMR spectrum shows an apparent singlet (doublet with J lower than 2 Hz), corresponding to four chemically equivalent $\beta$-protons coupled with the two pyrrolic protons which have lost their delocalization (Crossley et al, J. Chem. Soc., Chem. Commun. 1564 (1991). Nevertheless, another less polar fraction (R$_f$=0.60) was identified, according to its mass spectrum, as a mixture of other tetrachloro-regioisomers ($^1$H-NMR spectrum uninterpretable), representing approximately 50% by weight of both $\beta$-Cl$_4$ fractions, and showing that the $\beta$-substitution is only partially regioselective. According to the $^1$H-NMR spectrum of the corresponding H$_2$Cl$_3$T-2-PyP$^{5+}$ fraction, there are no apparent other regioisomers. The spectrum presents one singlet corresponding to the $\beta$-proton of the monosubstituted pyrrole and four doublets corresponding to the four $\beta$-protons of the two non-substituted pyrroles. Moreover, the asymmetry of this compound leads to a differentiation of the two NH protons. According to yields and $^1$H-NMR spectra of H$_2$Cl$_{2a}$T-2-PyP (FIG. 5) and H$_2$Cl$_{2b+2c}$T-2-PyP, no predominant $\beta$-Cl$_2$ regioisomer was observed. Finally, the H$_2$Cl$_1$T-2-PyP spectrum shows one singlet and six doublets, but only one NH signal, suggesting that in this case the asymmetry is too weak for the differentiation of the two NH protons.

TABLE 4

$H_2Cl_xT$-2-PyP (x = 1 to 4): $^1$H-NMR data (porphyrin ring) in $CDCl_3$

| | | $\delta_{ppm}$ (mult., Hz)$^a$ |
|---|---|---|
| $H_2Cl_1T$-2-PyP | NH | -2.91 (2H) |
| | CH | 7.68 (s, 1H) |
| | | 8.74 (d, 1H, 5.5) |
| | | 8.76 (d, 1H, 5.5) |
| | | 8.76 (d, 1H, 6.0) |
| | | 8.88 (d, 1H, 6.0) |
| | | 8.90 (d, 1H, 6.0) |
| | | 8.94 (d, 1H, 6.0) |
| $H_2Cl_{2a}T$-2PyP | NH | -2.98 (2H) |
| | CH | 8.70 (s, 2H) |
| | | 8.82 (d, 2H, 6 0) |
| | | 8.91 (d, 2H, 6 0) |
| $H_2Cl_{2b}T$-2-PyP$^b$ | NH | -3.04 (2H) |
| | CH | 8.59 (s, 2H) |
| | | 8.78 (d, 2H, 6.0) |
| | | 8.87 (d, 2H, 6.0) |
| $H_2Cl_{2c}T$-2-PyP$^b$ | NH | -2.84 (1H) |
| | | -2.87 (1H) |
| | CH | 8.61 (s, 2H) |
| | | 8.73 (d, 2H, <2.0) |
| | | 8.93 (d, 2H, <2.0) |
| $H_2Cl_3T$-2-PyP | NH | -3.08 (1H) |
| | | -3.15 (1H) |
| | CH | 8.56 (s, 1H) |
| | | 8.72 (d, 1H, 6.5) |
| | | 8.76 (d, 1H, 6.5) |
| | | 8.82 (d, 1H, 6.5) |
| | | 8.88 (d, 1H, 6.5) |
| $H_2Cl_4T$-2-PyP | NH | -3.14 (2H) |
| | CH | 8.74 (d, 4H, <2.0) |

$^a$chemical shifts in ppm expressed relative to TMS by setting $CDCl_3$ = 7.24 ppm.
$^b$one spectrum for the mixture of the two regioisomers (~1:1 ratio).

N-ethylation and metallation. The N-ethylation of $H_2$T-2-PyP was efficiently accomplished using ethyl-p-toluenesulfonate, diethylsulfate or iodoethane as reagents, but the high toxicity of diethylsulfate and the low reactivity of iodoethane makes ethyl-p-toluenesulfonate (ETS) the best choice (Chen et al, J. Electroanal. Chem. 280:189 (1990); Kalyamasundaram, Inorg. Chem. 23:2453 (1984); Hambright et al, Inorg. Chem. 15:1314 (1976); Alder et al, Chem. Brit. 14:324 (1978); Perree-Fauvet et al, 52:13569 (1996)). Some authors prefer performing N-alkylation after metallation in order to protect the pyrrole nitrogens (Perree-Fauvet et al, Tetrahedron 52:13569 (1996)). However, with direct treatment on the present free ligands, no N-ethylation of the pyrrole nitrogens was observed (subsequent metallation in aqueous solution was complete). The completion of ethylation as well as metallation can be followed by TLC (normal silica) using a highly polar eluant, a mixture of an aqueous solution of saturated potassium nitrate with acetonitrile (Batinic-Haberle et al, J. Biol. Chem. 273:24521 (1998)). The yields of this step (N-ethylation and metallation) were almost 100% (approximately 5% loss during the purification process). Since N-ethylation (or N-methylation) limits the free rotation of the pyridinium rings, each compound is in fact a mixture of four atropoisomers, and a further purification of each atropoisomer can be considered (Kaufmann et al, Inorg. Chem. 34:5073 (1995)). All the manganese porphyrins prepared had metal in the 3+ state as demonstrated by the 20 nm hypsochromic shift of the Soret band (accompanied by the loss of splitting) upon the reduction of the metal-center by ascorbic acid.

Electrochemistry. The metal-centered redox behavior of all metalloporphyrin products was reversible. The half-wave potentials ($E°_{1/2}$) were calculated as the average of the cathodic and anodic peaks and are given in mV vs NHE (Table 5). The average shift per chlorine is +55 mV (Table 5), which is in agreement with the values previously reported for $H_2$TPP derivatives (between +50 and +70 mV) (Sen et al, Chem. Soc. Faraday Trans. 93:4281 (1997); Autret et al, J. Chem. Soc. Dalton Trans. 2793 (1996); Hariprasad et al, J. Chem. Soc. Dalton Trans. 3429 (1996); Tagliatesta et al, Inorg. Chem. 35:5570 (1996); Ghosh, J. Am. Chem. Soc. 117:4691 (1995); Takeuchi et al, J. Am. Chem. Soc. 116:9730 (1994); Binstead et al, Inorg. Chem. 30:1259 (1991); Giraudeau et al, J. Am. Chem. Soc. 101:3857 (1979)). This shift appears to be higher (~+65 mV) between 0 and 1, and between 2 and 3 chlorines (Table 5). $E°_{1/2}$ values of $\beta$-$Cl_{2a}$ and the mixture $\beta$-$Cl_{2b+2c}$ were not significantly different. The manganese redox state of $MnCl_4TE$-2-PyP$^{5+}$ ($E°_{1/2}$=+448 mV) and MnOBTMPyP$^{4+}$ ($E°_{1/2}$=+480 mV) is 3+ and 2+, respectively. This difference may be explained by their difference in terms of redox potential (~30 mV) but also by structural considerations, for instance an increased distortion of the porphyrin ring in the case of MnOBTMPyP$^{4+}$. (Batinic-Haberle et al, Arch. Biochem. Biophys. 343:225 (1997); Ochsenbein et al, Angew. Chem. Int. Ed. Engl. 33:348 (1994)).

TABLE 5

$MnCl_xTE$-2-PyP$^{5-}$ (x = 1 to 4): Soret band data, redox potentials and SOD activities.

| Mn-porphyrin | $\lambda$nm ($\epsilon/10^4$ M$^{-1}$ cm$^{-1}$)$^a$ | $E°_{1/2}$ ($\Delta$)$^b$ | $IC_{50}/10^{-9}$ M$^c$ | $k_{cat}/10^7$ M$^{-1}$s$^{-1}$ |
|---|---|---|---|---|
| MnTE-2-PyP$^{5-}$ | 453.8 (14.0) | +228 (71) | 45 | 5.7 |
| $\beta$-$Cl_1$ | 455.6 (12.5) | +293 (65) | 25 | 10 |
| $\beta$-$Cl_{2a}$ | 456.4 (10.6) | +342 (70) | 20 | 13 |
| $\beta$-$Cl_{2b-2c}$ | 457.4 (11.2) | +344 (65) | 20 | 13 |
| $\beta$-$Cl_3$ | 458.0 (9 5) | +408 (67) | 10 | 26 |
| $\beta$-$Cl_4$ | 459 2 (8.0) | +448 (79) | 6.5 | 40 |
| MnTM-4-PyP$^{5-}$ | | +060 | | 0.4 |
| MnTM-2-PyP$^{5-}$ | | +220 | | 6.0 |
| MnOBTMPyP$^{4+}$ | | +480 | | 22 |
| Cu,ZnSOD | | +260 | | 200 |

$^a$in $H_2O$ (estimated errors for $\epsilon$ are within ±10%).
$^b$mV vs NHE, with estimated errors of ±5 mV ($\Delta$ = peak to peak separation), and in the following conditions: 0.5 mM porphyrin, 0.1M NaCl, 0.05M phosphate buffer (pH 7.8).
$^c$concentration that causes 50% inhibition of cytochrome c reduction by $O_2^-$ (estimated errors are within ±10%).

Superoxide dismuting activities. SOD-like activities were measured as described previously, based on competition with cytochrome c (McCord et al, J. Biol. Chem. 244:6049 (1969)). $MnCl_xTE$-2-$PyP^{5+}$ SOD-like activities are reported in Table 5, $IC_{50}$ (M) representing the concentration for one unit of activity (or the concentration that causes 50% inhibition of cytochrome c reduction by $O_2^-$) and $k_{cat}$ ($M^{-1}s^{-1}$) representing the rate constant for the superoxide dismutation reaction. The SOD-like activity per mole of $MnCl_4TE$-2-$PyP^{5+}$ is approximately 2-, 7- and 100-fold higher than $MnOBTMPyP^{4+}$, $MnTM$-2-$PyP^{5+}$ and $MnTM$-4-$PyP^{5+}$, respectively (Faulkner et al, J. Biol. Chem. 269:23471 (1994); Batinic-Haberle et al, Arch. Biochem. Biophys. 343:225 (1997); Batinic-Haberle et al, J. Biol. Chem. 273:24521 (1998)). The SOD-like activity of $MnCl_4TE$-2-$PyP^{5+}$ represents 20% of the activity of the Cu,Zn-SOD enzyme on a molar basis (40% per active site considering that the enzyme has two active sites) (Klug-Roth et al, J. Am. Chem. Soc. 95:2786 (1973)).

Test of stability. Each additional degree of chlorination increases the redox potential which is expected to be followed by the decrease in the pKa values of pyrrole nitrogens, as found for the series of meso-phenyl and meso-pyridyl substituted porphyrins as well as for β-substituted ones (Worthington et al, Inorg. Nucl. Chem. Lett. 16:441 (1980); Kadish et al, Inorg. Chem. 15:980 (1976)). The pKa, as a measure of the ligand-proton stability, is in turn a measure of the metal-ligand stability as well. Thus, the tetrachloro-compound is expected to be of decreased stability as compared to lesser chlorinated analogues. The stability of $MnCl_4TE$-2-$PyP^{5+}$ was tested by measuring its SOD-like activity in the presence of excess EDTA. In the presence of a $10^2$-fold excess of EDTA, $MnCl_4TE$-2-$PyP^{5+}$ (c=$5\times10^{-6}$ M) maintains its activity for sixteen hours (at 25° C.). A loss of activity (~25%) was observed after forty hours, thus indicating the formation of some manganese—EDTA complex (K=$10^{14.05}$). These results confirm a relatively good stability of $MnCl_4TE$-2-$PyP^{5+}$ when compared to $MnOBTMPyP^{4+}$ (K=$10^{8.08}$) (Batinic-Haberle et al, Arch. Biochem. Biophys. 343:225 (1997)).

Relationship between redox properties and SOD-like activities. The Cu,Zn-SOD enzyme is a dimer of two identical subunits, and thus has two active sites, which exhibit a redox potential close to the midpoint of the two half reaction values, as well as the same rate constants for each half reaction (Scheme C and Table 5) (Ellerby et al, J. am. Chem. Soc. 118:6556 (1996); Klug-Roth, J. Am. Chem. Soc. 95:2786 (1973)):

Scheme C

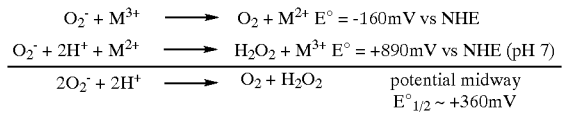

Figure 6:
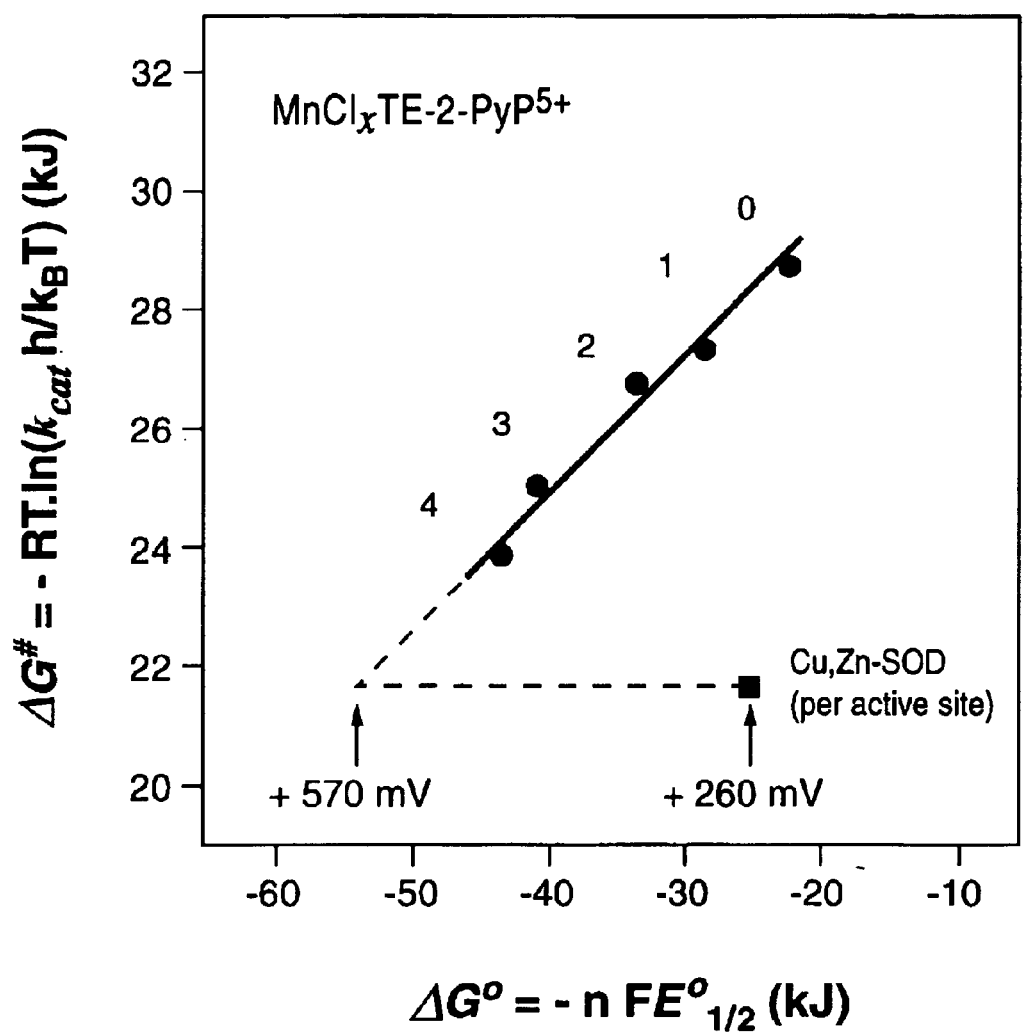
FIG. 6. Plot of the free energy of activation ($\Delta G^\#$) for the $O_2^-$ dismutation reaction catalyzed by $MnCl_xTE\text{-}2\text{-}PyP^{5+}$ as a function of the ground state free energy change ($\Delta G^\circ$) for $MnCl_xTE\text{-}2\text{-}PyP^{5+}$ redox. $\Delta G^\#$ and $\Delta G^\circ$ were calculated from $k_{cat}$ and $E^\circ_{1/2}$ values reported in Table 4 (E, R, h and $k_B$ are Faraday, molar gas, Planck and Boltzmann constants, respectively).

On the other hand, previous studies of $O_2^-$ dismutation catalyzed by $MnTM$-4-$PyP^{5+}$ ($E°_{1/2}$=+60 mV), using pulse radiolysis and stopped flow techniques, showed that the rate of the reduction of the metal by $O_2^-$ is $10^2$-fold to $10^3$-fold lower than the rate of reoxidation of the metal (Faraggi, Oxygen Radicals in Chemistry and Biology, Bors et al (Eds): Walter de Gruyter and Co.; Berlin, Germany 1984, p. 419; Lee et al, J. Am. Chem. Soc. 120:6053 (1998)). Whereas a peak of SOD-like activity somewhere between +200 and +450 mV was first expected, plotting $k_{cat}$ vs $E°_{1/2}$ for $MnCl_xTE$-2-$PyP^{5+}$ shows an exponential increase of the SOD-like activity, strongly suggesting that the limiting factor is still the reduction of the metal. This hypothesis however must be confirmed by measuring the rates of each half reaction as catalyzed by each $MnCl_xTE$-2-$PyP^{5+}$ compound. The relationship between activation free energy ($\Delta G^{\#}$) for superoxide dismutation and free energy change ($\Delta G°$) for $MnCl_xTE$-2-$PyP^{5+}$ redox is linear (slope ~+0.2), clearly showing the predominance of kinetic over thermodynamic factors in the theoretical optimal redox potential region (FIG. 6). According to this behavior, the activity of the Cu,Zn-SOD enzyme ($k_{cat}$=$10^9$ $M^{-1}s^{-1}$ per active site) may be reached at approximately $E°_{1/2}$=+570 mV (FIG. 3). However, due to both steric (distortion of the porphyrin ring) and thermodynamic factors, introducing a higher degree of β-chlorination is expected to stabilize the manganese in the 2+ redox state, and thus, as in the case of $MnOBTMPyP^{4+}$, limiting the rate of the reoxidation of the metal as well as inducing Mn(II) dissociation (Batinic-Haberle et al, Arch. Biochem. Biophys. 343:225 (1997); Ochsenbein et al, Angew. Chem. Int. Ed. Engl. 33:348 (1994)).

Example VII

The ortho, meta and para isomers of manganese(III) 5,10,15,20-tetrakis(N-methylpyridyl)porphyrin, $MnTM$-2-$PyP^{5+}$, $MnTM$-3-$PyP^{5+}$, and $MnTM$-4-$PyP^{5+}$, respectively, were analyzed in terms of their superoxide dismutase (SOD) activity in vitro and in vivo. The impact of their interaction with DNA and RNA on the SOD activity in vivo and in vitro was also analyzed. Differences in their behavior are due to the combined steric and electrostatic factors. In vitro catalytic activities are closely related to their redox potentials. The half-wave potentials ($E_{1/2}$) are +0.220 mV, +0.052 mV and +0.060 V vs normal hydrogen electrode (NHE), while the rates of dismutation ($k_{cat}$) are $6.0\times10^7$ $M^{-1}$ $s^{-1}$, $4.1\times10^6$ $M^{-1}s^{-1}$ and $3.8\times10^6$ $M^{-1}$ $s^{-1}$ for the ortho, meta and para isomers, respectively.

However, the in vitro activity is not a sufficient predictor of in vivo efficacy. The ortho and meta isomers, although of significantly different in vitro SOD activities, have fairly close in vivo SOD efficacy due to their similarly weak interactions with DNA. In contrast, due to a higher degree of interaction with DNA, the para isomer inhibited growth of SOD-deficient Escherichia coli. For details, see Batinic-Haberle et al, J. Biol. Chem. 273(38):24521–8 (Sep. 18, 1998).

Example VIII

Metalloporphyrins are Potent Inhibitors of Lipid Peroxidation

Materials and Methods

L-Ascorbic acid, n-butanol, butylated hydroxytoluene, cobalt chloride, iron(II) chloride, phosphoric acid (85%), sodium hydroxide, potassium phosphate, tetrabutylammonium chloride, and 1,1,3,3-tetramethoxypropane were purchased from Sigma (St. Louis, Mo.). Acetone, concentrated hydrochloric acid, 4,6-dihydroxy-2-mercaptopyrimidine (thiobarbituric acid), $NH_4PF_6$, zinc chloride, 5,10,15,20-tetrakis (4-benzoic acid) porphyrin ($H_2TBAP$)*, 5,10,15,20-tetrakis (N-methylpyridinium-4-yl) porphyrin ($H_2TM$-4-$PyP$), and Trolox were purchased from Aldrich (Milwaukee, Wisc.). Ferric 5,10,15,20-tetrakis (4-benzoic acid) porphyrin (FeTBAP) was purchased from Porphyrin Products (Logan, Utah). 5,10,15,20-tetrakis (N-methylpyridinium-2-yl) porphyrin ($H_2TM$-2-$PyP$) was purchased from MidCentury Chemicals (Posen, Ill.). (+)-Rutin was purchased from Calbiochem (La Jolla, Calif.). Manganese chloride was purchased from Fisher (Fair Lawn, N.J.) and ethanol USP was purchased from AAPER Alcohol and Chemical Co. (Shelbville, Ky.). All solutions were prepared in Milli-Q Plus PF water (Millipore, Bedford, Mass.).

* Also known as 5,10,15,20-tetrakis (4-carboxyphenyl) porphyrin ($H_2$TCPP)

Preparation and Analysis of Metalloporphyrins

The metalloporphyrins MnTBAP, CoTBAP and ZnTBAP were made using methods described previously (Day et al, J. Pharmacol. Exp. Ther. 275:1227 (1995)). MnTM-4-PyP, CoTM-4-PyP and ZnTM-4-PyP were synthesized by the following method. A 1.5 molar excess of manganese, cobalt or zinc chloride was mixed with $H_2$TM-4-PyP that was dissolved in de-ionized water. The reaction mixture was heated to 80° C. and metal ligation was followed spectrophotometrically (UV-2401PC, Shimadzu, Columbia, Md.). Excess metal was removed by passing the mixture through a column containing Bio-Gel P-2 (BioRad, Richmond, Calif.) that selectively retained MnTM-4-PyP. MnTM-4-PyP was eluted with 0.01 N HCl after extensive washing of the column with water. MnTM-4-PyP, CoTM-4-PyP and ZnTM-4-PyP were characterized in terms of their reported Soret bands. The Soret band for MnTM-4-PyP is at 463 nm with an extinction coefficient of $(\epsilon)=1.3\times10^5$ $M^{-1}$ $cm^{-1}$, the Soret band for ZnTM-4-PyP is at 437 nm with an extinction coefficient of $(\epsilon)=2.0\times10^5$ $M^{-1}$ $cm^{-1}$ (Pasternack et al, Inorg. Chem. 12:2606 (1973)) and the Soret band for CoTM-4-PyP is at 434 nm with an extinction coefficient of $(\epsilon)=2.15\times10^5$ $M^{-1}cm^{-1}$ (Pasternack et al, Biochemistry 22:2406 (1983)). Manganese β-octabromo-meso-tetrakis-(N-methylpyridinium-4-yl) porphyrin (MnOBTM-4-PyP) was synthesized as previously described (Batinic-Haberle et al, Arch. Biochem. Biophys. 343:225 (1997)) and has a Soret band at 490 nm with an extinction coefficient $(\epsilon)=8.56\times10^4$ $M^{-1}$ $cm^{-1}$. $H_2$TM-2-PyP was metallated with a 1:20 porphyrin to manganese ratio in water (pH>11) at room temperature. Upon completion of metallation, MnTM-2-PyP was precipitated by the addition of a concentrated aqueous solution of $NH_4PF_6$. The precipitate was washed with 2-propanol:diethyl ether (1:1) and dried in vacuo at room temperature. The $PF_6^-$ salt of MnTM-2-PyP was dissolved in acetone, filtered and a concentrated acetone solution of tetrabutylammonium chloride was added until the porphyrin had precipitated as its chloride salt. The precipitate was washed with acetone and dried in vacuo at room temperature. The Soret band for MnTM-2-PyP was found at 453 nm with an extinction coefficient $(\epsilon)=1.29\times10^5$ $M^{-1}$ $cm^{-1}$.

Preparation of Rat Brain Homogenates

Frozen adult Sprague-Dawley rat brains (Pel-Freez, Rogers, Ariz.) were homogenized with a polytron (Turrax T25, Germany) in 5 volumes of ice cold 50 mM potassium phosphate at pH 7.4. Homogenate protein concentration was determined with the Coomassie Plus protein assay (Pierce, Rockford, Ill.) using bovine serum albumin as a standard. The homogenate volume was adjusted with buffer to give a final protein concentration of 10 mg/ml and frozen as aliquots at –80° C.

Oxidation of Rat Brain Homogenates

Rat brain homogenates (2 mg protein) were incubated with varying concentrations of antioxidant at 37° C. for 15 minutes. Oxidation of the rat brain homogenate was initiated by the addition of 0.1 ml of a freshly prepared anaerobic stock solution containing iron(II) chloride (0.25 mM) and ascorbate (1 mM) as previously reported (Braughler et al, J. Biol. Chem. 262:10438 (1987)). Samples (final volume 1 ml) were placed in a shaking water bath at 37° C. for 30 minutes. The reactions were stopped by the addition of 0.1 ml of a stock butylated hydroxytoluene (60 mM) solution in ethanol.

Lipid Peroxidation Measurement

The concentration of thiobarbituric acid reactive species (TBARS) in rat brain homogenates was used as a index of lipid peroxidation (Bernhem et al, J. Biol. Chem. 174:257 (1948); Witz et al, J. Free Rad. Biol. Med. 2:33 (1986); Kikugawa et al, Anal. Biochem. 202:249 (1992); Jentzsch et all Free Rad. Biol. Med. 20P251 (1996)). Malondialdehyde standards were obtained by adding 8.2 µl of 1,1,3,3-tetramethoxypropane in 10 ml of 0.01 M HCl and mixing for 10 minutes at room temperature. This stock was further diluted in water to give standards that ranged from 0.25 to 25 µM. Samples or standards (200 µl) were acidified with 200 µl of 0.2 M phosphoric acid in 1.5 ml locking microfuge tubes. The color reaction was initiated by the addition of 25 µl of a 0.11M thiobarbituric acid solution and samples were placed in a 90° C. heating block for 45 minutes. TBARS were extracted with 0.5 ml of n-butanol by vortexing samples for 3 minute and chilling on ice for 1 minute. The samples were then centrifuged at 12,000×g for 3 minutes, 150 µl aliquots of the n-butanol phase were placed in each well of a 96-well plate and read at 535 nm in a Thermomax platereader (Molecular Devices, Sunnyvale, Calif.) at 25° C. Sample absorbencies were converted to MDA equivalencies (µM) by extrapolation from the MDA standard curve. None of the antioxidants at concentrations employed in these studies affected the reaction of MDA standards with thiobarbituric acid and reactions without TBA were used as subtraction blanks.

Statistical Analyses

Data were presented as their means ±SE. The inhibitory concentration of antioxidants that decreased the degree of lipid peroxidation by 50% ($IC_{50}$) and respective 95% confidence intervals (CI) were determined by fitting a sigmoidal curve with variable slope to the data (GraphPad Prizm, San Diego, Calif.).

Results

Comparison of Metalloporphyrins with Other Antioxidants in Iron/Ascorbate-mediated Lipid Peroxidation The objective of these studies was to investigate whether metalloporphyrins could inhibit lipid peroxidation and to compare their potencies with those of previously characterized antioxidants that include enzymatic antioxidants (SOD and catalase) and non-enzymatic antioxidants (water soluble vitamin E analog, trolox, and plant polyphenolic flavonoid, rutin) (FIG. 7). The time course of lipid peroxidation was determined in rat brain homogenates using iron and ascorbate as initiators of lipid oxidation and the formation of thiobarbituric reactive species (TBARS) as an index of lipid peroxidation. A linear increase in the formation of TBARS occurred between 15 to 90 minutes of incubation at 37° C. (FIG. 8). Based on this result, an incubation time of 30 minutes was selected to test the ability of metalloporphyrins and other antioxidants to inhibit lipid peroxidation. (FIG. 9). Of the agents tested, the manganese porphyrins that have the highest SOD activities, MnOBTM-4-PyP and MnTM-2-PyP, were found to be the most potent lipid peroxidation inhibitors with calculated $IC_{50}$s of 1.3 and 1.0 µM respectively. (Table 6). Bovine CuZnSOD was moderately active with a calculated $IC_{50}$ of 15 µM while trolox and rutin were much less potent with calculated $IC_{50}$s of 204 and 112 µM, respectively. In this system, catalase (up to concentrations of 1 mg/ml) did not inhibit iron/ascorbate-initiated lipid peroxidation.

TABLE 6

Comparison of Antioxidant Properties

| Antioxidants | SOD (U/mg)[a] | Redox Potential ($E_{1/2}$, V)[b] | Lipid Peroxidation[c] | |
|---|---|---|---|---|
| | | | $IC_{50}$ [µM] | 95% CI [µM] |
| CuZnSOD | 5,100 | +0.35 | 15 | 13–17 |
| Trolox | — | — | 204 | 135–308 |
| Rutin | — | — | 113 | 99–129 |
| MnTM-2-PyP | 8,500 | +0.22 | 1.0 | 0.4–2.2 |
| MnOBTM-4-PyP | 18,460 | +0.48 | 1.3 | 0.8–2.2 |
| MnTM-4-PyP | 547 | +0.06 | 16 | 12–22 |
| MnTBAP | 179 | −0.19 | 29 | 23–37 |
| CoTM-4-PyP | 113 | +0.42 | 17 | 14–22 |
| CoTBAP | 24 | +0.20 | 21 | 13–33 |
| FeTBAP | 24 | +0.01 | 212 | 144–311 |
| ZnTM-4-PyP | trace | — | 241 | 159–364 |
| ZnTM-2-PyP | trace | — | 591 | 423–827 |
| ZnTBAP | trace | — | 843 | 428–1660 |

[a]Unit of SOD activity defined as the amount of compound that inhibits one half the reduction of cytochrome c or photoreduction of NBT.
[b]Metal centered redox potentials vs NHE ($Mn^{+3}/Mn^{+2}$; $Co^{+3}/Co^{+2}$; $Fe^{+3}/Fe^{+2}$). If not otherwise specified, $E_{1/2}$ were obtained at pH 7.8.
[c]The amount of thiobarbaturic acid reactive substances produced in a rat brain homogenate by 30 minutes of incubation of iron and ascorbate.

Effect of Different Metal Chelates on the Ability of Porphyrins to Inhibit Lipid Peroxidation A wide range of metals can be covalently ligated by porphyrins and that confers different redox potentials and SOD activities (Table 6). The ability of different metal chelates to influence a porphyrin's ability to inhibit lipid peroxidation was tested. Several different metal analogs of TBAP were examined in the iron/ascorbate-initiated lipid peroxidation model (FIG. 10). Both the manganese and cobalt TBAP analogs had similar efficacy with calculated $IC_{50}$ of 29 and 21 µM, respectively. The FeTBAP analog was an order of magnitude less potent with a calculated $IC_{50}$ of 212 µM. The ZnTBAP analog was much less active than the other metal analogs with a calculated $IC_{50}$ of 946 µM. This potency difference between the zinc and the other metals reflects the importance of metal centered verses ring structure redox chemistry since zinc can not readily change its valence. The ranked potencies of tested metalloporphyrins based on $IC_{50}$s were as follows: MnTM-2-PyP=MnOBTM-4-PyP>MnTM-4-PyP=CoTM-4-PyP>CoTBAP=MnTBAP>FeTBAP=ZnTM-4-PyP>ZnTM-2-PyP>ZnTBAP.

Comparison of a Series of Tetrakis N-methylpyridyl Porphyrin (TMPyP) Analogs as Inhibitors of Lipid Peroxidation Recently, several manganese analogs of N-methylpyridyl porphyrins have been found to possess large differences in SOD activities (Table 6). MnTM-2-PyP and MnTM-4-PyP differ structurally with respect to the position of the N-methylpyridyl group to the porphyrin ring (ortho vs para) as well as in SOD activity by a factor of six. Substitution of zinc in these porphyrin analogs results in loss of SOD activity. These TMPyP analogs were compared for their ability to inhibit lipid peroxidation (FIG. 11). The movement of the N-methylpyridyl group from the para- to the ortho-position in the manganese porphyrin resulted in a 15-fold increase in potency. Since MnTM-2-PyP possesses a more positive redox potential than MnTM-4-PyP (+0.22 vs +0.06, respectively), this data suggests that both the redox potential and the related SOD activity may contribute to the increased potency of the MnTM-2-PyP analog.

Example IX

Demonstration that Mn TE-2-PyP can be Effectively Used to Attenuate Oxidant Stress Mediated Tissue Injury The ability of Mn TE-2-PyP to attenuate injury associated with 60 minutes of global ischemia followed by 90 minutes of reperfusion was assessed in an isolated, perfused mouse liver model. Excised livers were perfused with a buffered salt solution for 15 minutes after which the metalloporphyrin was introduced into the perfusate and the liver perfused in a recirculating system for an additional 15 minutes. The livers were then rendered globally ischemic under normal thermic conditions for 60 minutes. Following the ischemic period the livers were perfused for 90 minutes with perfusate supplemented with 10 µm Mn TE-2-PyP. In this model the ischemia/reperfused livers have a marked release of hepatocellular enzymes, aspartate transaminase, alanine transaminase, and lactate dehydrogenase during the first 2½ minutes of reperfusion. This is followed by a progressive release of hepatocellular enzymes indicating hepatocellular injury over the 90 minute perfusion period. Administration of Mn TE-2-PyP was highly efficacious in attenuating the liver injury, blocking virtually all of the acute hepatocellular enzyme release and blocking progressive hepatocellular enzyme release over the 90 minute perfusion period. At the end of the experiments liver is treated with the metalloporphyrin. It has demonstrated excellent oxygen consumption and a normal perfusion pattern. They remain firm and with a normal texture to gross morphologic examination. Livers with no drug treatment did not consume oxygen normally and became edematous, soft, and had a mottled appearance consistent with poor perfusion.

Example X

Effects of Mn TM-2-PyP on Vascular Tone

Rats were anesthetized and a femoral vein and carotid artery were cannulated. While blood pressure was monitored by the carotid artery, Mn TM-2-PyP was injected i.v. at doses ranging from 0.1 to 3.0 mg/kg. Mean arterial pressure fell from 100–125 mmHg to 50–60 mmHg within five to ten minutes. The effect was transient, lasting up to 30 minutes at doses of 0.1 to 0.25 mg/kg. At doses of 1–3 mg/kg the effect was prolonged, lasting up to two hours. The effect can be blocked by administration of inhibitors of nitric oxide synthase demonstrating that the role of Mn TM-2-PyP is being modulated by nitric oxide. Scavenging of superoxide in vascular walls would potentiate the effects of nitric oxide producing hypotension.

Example XI

Regulation of Airway Reactivity Using Mn TM-2-PyP

Mice were sensitized by intraperitoneal injection of ovalbumin twice, 14 days apart. Fourteen days after the second i.p. injection they were challenged with aerosolized ovalbumin daily for three days. Forty-eight hours after the third inhalation of ovalbumin they were given a 1 minute methacholine challenge and airway hyperreactivity followed using a Buxco body plethysmograph. Significant increases in airway resistance as measured by the PENH index occurred at doses of 20, 30 and 40 mg/ml of methacholine. At all doses of methacholine prior intratracheal instillations of 2 µg Mn TM-2-PyP given daily for 4 days resulted in a statistically significant reduction in the airway hyperreactivity. This dose of Mn TM-2-PyP is equivalent to 0.8 mg/kg whole body dose.

Example XII

Treatment of Bronchopulmonary Dysplasia Using Mn TE-2-PyP

Neonatal baboons were delivered prematurely by Caesarian section and then treated either with 100% oxygen or only sufficient PRN FIO$_2$ to maintain adequate arterial oxygenation. To establish the model, thirteen 100% oxygen treated animals and twelve PRN control animals were studied. Treatment with 100% oxygen results in extensive lung injury manifested by days 9 or 10 of exposure and characterized by delayed alveolarization, lung parenchymal inflammation, and poor oxygenation. This is characteristic of the human disease, bronchopulmonary dysplasia and is thought to be mediated, at least in part, by oxidative stress on the developing neonatal lung. In a first trial of Mn TE-2-PyP, a neonatal baboon was delivered at 140 days gestation and placed in 100% oxygen. The animal received 0.5 mg/kg/24 hr Mn TE-2-PyP qd given i.v. in a continuous infusion over the entire 10 day study period. This animal showed marked improvement of the oxygenation index. There was no evidence of clinical decompensation of the lungs at days 9 and 10. Lung pathology demonstrated absence of inflammation and a marked decrease in the lung injury found in the prior animals treated with 100% oxygen under identical conditions. This suggests that Mn TE-2-PyP can be used to treat oxidant stress in the premature newborn.

All documents cited above are hereby incorporated in their entirety by reference. Application Ser. No. 60/064,116, filed Nov. 3, 1997, is also incorporated in its entirety by reference.

One skilled in the art will appreciate from a reading of this disclosure that various changes in form and detail can be made without departing from the true scope of the invention.

What is claimed is:

1. A compound of formula

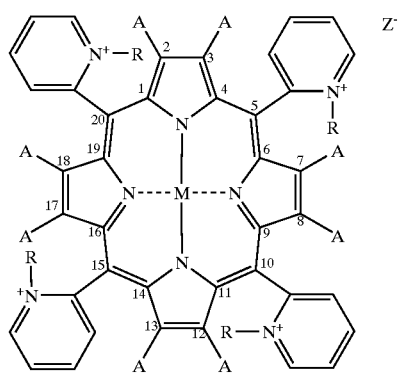

I

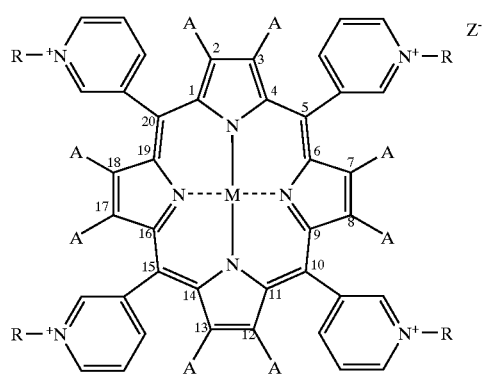

II

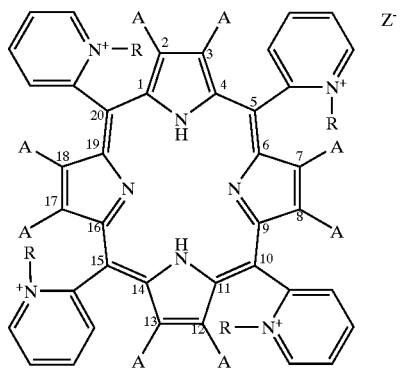

III or

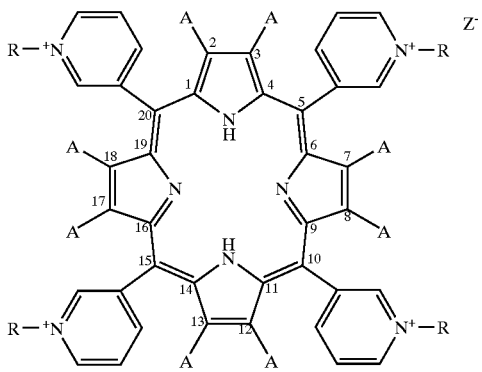

IV wherein each R is, independently, ethyl or isopropyl, each A is, independently, hydrogen or a halogen, M is a metal selected from the group consisting of manganese, iron, copper, cobalt, and nickel, and Z$^-$ is a counterion.

2. The compound according to claim 1 wherein each R is ethyl.

3. The compound according to claim 1 wherein at least one A is a halogen.

4. The compound according to claim 1 wherein said compound is of Formula I or II and M is manganese.

5. The compound according to claim 1 wherein said compound is of Formula I or III.

6. The compound according to claim 5 wherein said compound is of Formula I and M is manganese.

7. The compound according to claim 1 wherein said compound is a mixture of atropoisomers αααα, αααβ, ααββ and αβαβ.

8. The compound according to claim 1 wherein said compound is a mixture of αααβ and αααα atropoisomers.

9. A method of protecting cells from oxidant-induced toxicity comprising contacting said cells with a protective amount of a compound of formula

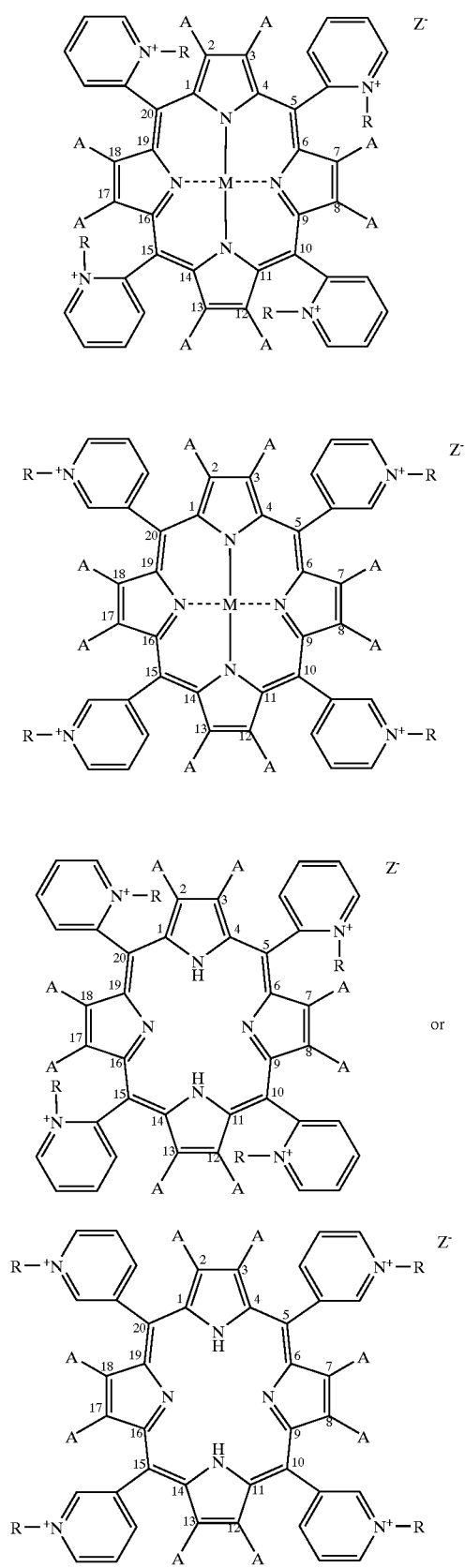

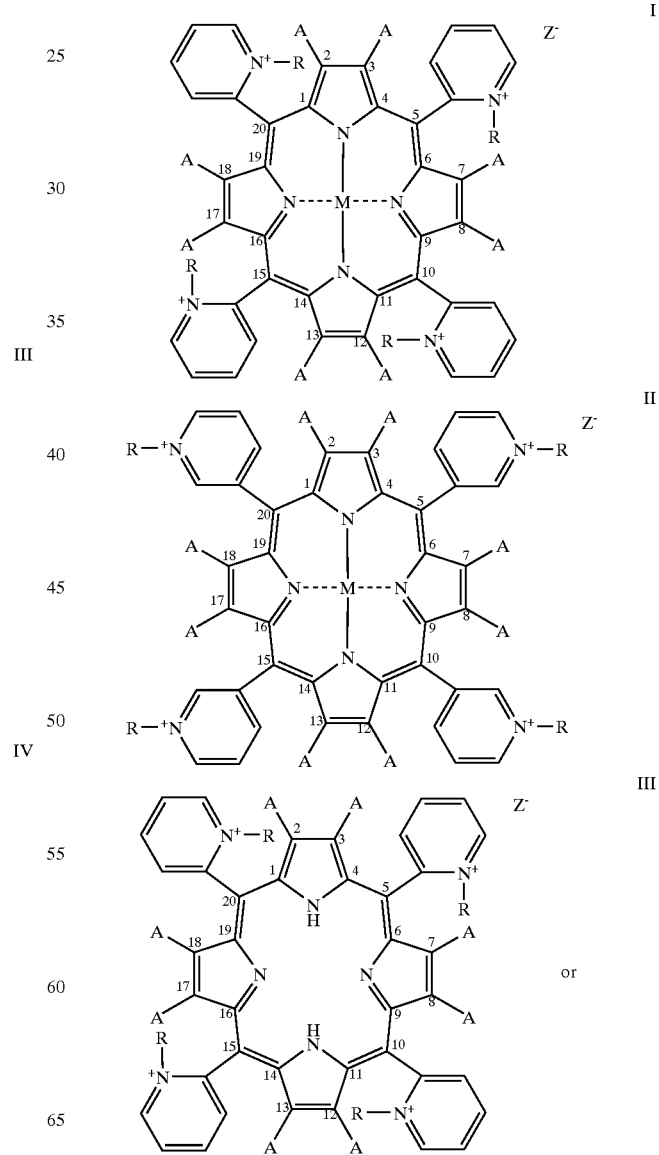

wherein each R is, independently, a $C_1$–$C_8$ alkyl group each A is, independently, hydrogen or a halogen, , M is a metal selected from the group consisting of manganese, iron, copper, cobalt, and nickel, and $Z^-$ is a counterion.

10. The method according to claim 9 wherein said cells are mammalian cells.

11. The method according to claim 9 wherein said compound is of Formula I or II and M is manganese.

12. The method according to claim 9 wherein said compound is of Formula I or III.

13. The method according to claim 12 wherein said compound is of Formula I and M is manganese.

14. The method according to claim 9 wherein each R is independently ethyl or isopropyl.

15. A method of treating a pathological condition of a patient resulting from oxidant-induced toxicity comprising administering to said patient an effective amount of a compound of formula

,

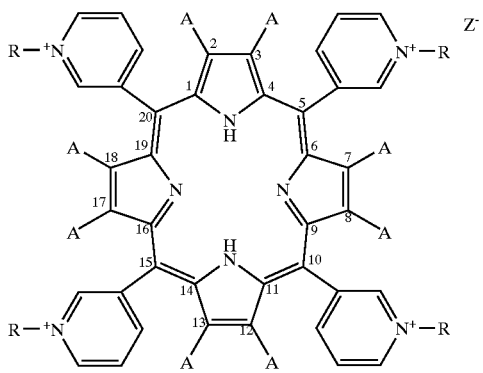

IV

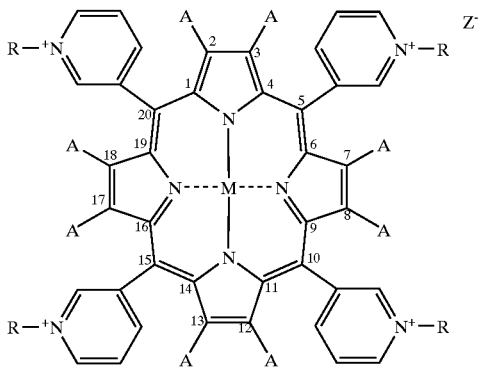

II wherein each R is, independently, a $C_1$–$C_8$ alkyl group, each A is, independently, hydrogen or a halogen, M is a metal selected from the group consisting of manganese, iron, copper, cobalt, and nickel, and $Z^-$ is a counterion.

16. The method according to claim 15 wherein said compound is of Formula I or II and M is manganese.

17. The method according to claim 15 wherein said compound is of Formula I or III.

18. The method according to claim 17 wherein said compound is of Formula I and M is manganese.

19. The method according to claim 15 wherein each R is independently ethyl or isopropyl.

20. A method of treating a pathological condition of a patient resulting from degradation of NO·, comprising administering to said patient an effective amount of a compound of formula

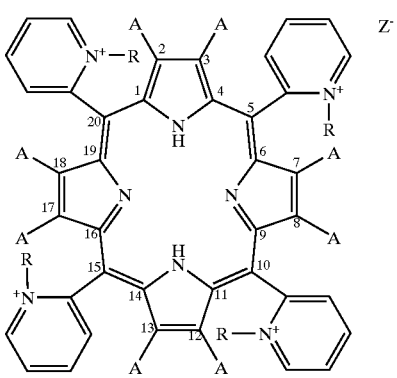

or

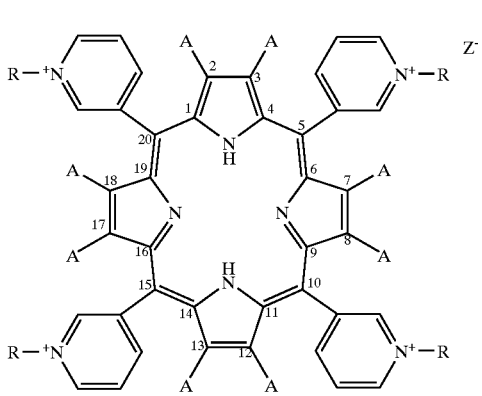

IV

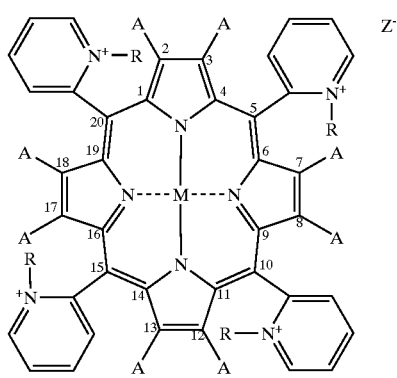

I wherein
each R is, independently, a $C_1$–$C_8$ alkyl group, and
each A is, independently, hydrogen or a halogen,
M is a metal selected from the group consisting of manganese, iron, copper, cobalt, and nickel, and
Z– is a counterion.

21. The method according to claim 20 wherein said compound is of Formula I or II and M is manganese.

22. The method according to claim 20 wherein said compound is of Formula I or III.

23. The method according to claim 22 wherein said compound is of Formula I and M is manganese.

24. The method according to claim 20 wherein each R is independently ethyl or isopropyl.

25. A method of treating a patient for inflammatory lung disease comprising administering to said patient an effective amount of a compound of formula

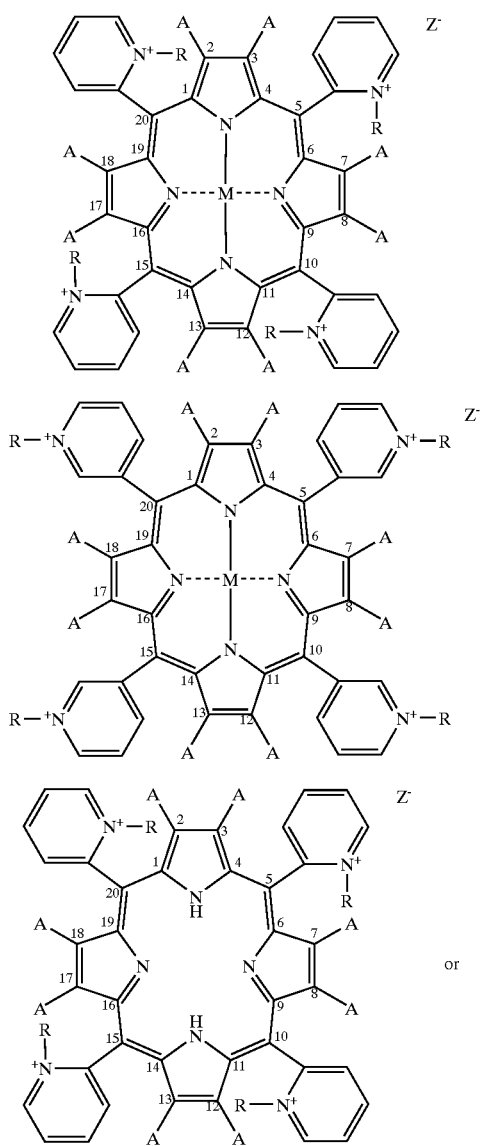

-continued

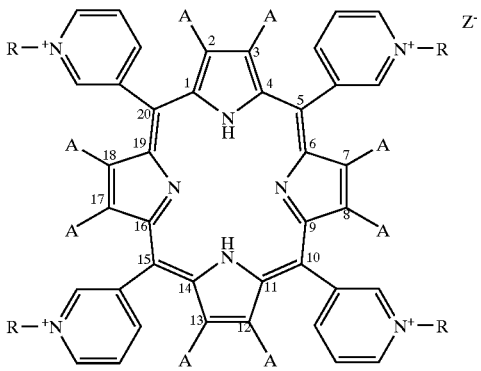

wherein each R is, independently, a $C_1$–$C_8$ alkyl group, and each A is, independently, hydrogen or a halogen, M is a metal selected from the group consisting of manganese, iron, copper, cobalt, and nickel, and $Z^-$ is a counterion.

26. The method according to claim 25 wherein said compound is of Formula I or II and M is manganese.

27. The method according to claim 25 wherein said inflammatory lung disease is a hyperreactive airway disease.

28. The method according to claim 25 wherein said inflammatory lung disease is asthma.

29. The method according to claim 25 wherein said compound is of Formula I or II and M is manganese.

30. The method according to claim 25 wherein said compound is of Formula I or III.

31. The method according to claim 30 wherein said compound is of Formula I and M is manganese.

32. The method according to claim 25 wherein each R is independently methyl, ethyl or isopropyl.

* * * * *